US009469630B2

(12) United States Patent
Nakagawa et al.

(10) Patent No.: US 9,469,630 B2
(45) Date of Patent: Oct. 18, 2016

(54) SUSTAINED-RELEASE FORMULATION FOR INJECTION

(75) Inventors: Takashi Nakagawa, Osaka (JP); Norimasa Koseki, Osaka (JP)

(73) Assignee: SUMITOMO DAINIPPON PHARMA CO., LTD., Osaka-shi (JP)

(*) Notice: Subject to any disclaimer, the term of this patent is extended or adjusted under 35 U.S.C. 154(b) by 0 days.

(21) Appl. No.: 13/276,039

(22) Filed: Oct. 18, 2011

(65) Prior Publication Data

US 2012/0091022 A1    Apr. 19, 2012

Related U.S. Application Data

(60) Provisional application No. 61/394,069, filed on Oct. 18, 2010.

(51) Int. Cl.

| A61K 31/497 | (2006.01) |
|---|---|
| C07D 417/12 | (2006.01) |
| A61K 31/496 | (2006.01) |
| A61K 9/00 | (2006.01) |
| A61K 47/02 | (2006.01) |
| A61K 47/26 | (2006.01) |
| A61K 9/10 | (2006.01) |

(52) U.S. Cl.
CPC ........... *C07D 417/12* (2013.01); *A61K 9/0019* (2013.01); *A61K 9/10* (2013.01); *A61K 31/496* (2013.01); *A61K 47/02* (2013.01); *A61K 47/26* (2013.01)

(58) Field of Classification Search
None
See application file for complete search history.

(56) References Cited

U.S. PATENT DOCUMENTS

| 5,532,372 | A | 7/1996 | Saji et al. | |
|---|---|---|---|---|
| 6,077,843 | A | 6/2000 | François | |
| 6,495,164 | B1 | 12/2002 | Ramstack et al. | |
| 6,616,945 | B1 | 9/2003 | Lankinen | |
| 8,227,488 | B2 * | 7/2012 | Wieckhusen et al. | 514/320 |
| 2003/0027816 | A1 | 2/2003 | Allen et al. | |
| 2003/0064998 | A1 | 4/2003 | Francois et al. | |
| 2003/0215517 | A1 | 11/2003 | Grawe et al. | |
| 2004/0022862 | A1 | 2/2004 | Kipp et al. | |
| 2005/0148597 | A1 | 7/2005 | Kostanski et al. | |
| 2005/0152981 | A1 | 7/2005 | Gleeson et al. | |
| 2005/0250813 | A1 | 11/2005 | Wieckhusen et al. | |
| 2006/0154918 | A1 | 7/2006 | Liversidge et al. | |
| 2006/0194970 | A1 | 8/2006 | Kakiya et al. | |
| 2007/0148100 | A1 | 6/2007 | Jenkins | |
| 2008/0096871 | A1 | 4/2008 | Bush | |
| 2008/0193542 | A1 | 8/2008 | Shah et al. | |
| 2009/0087492 | A1 | 4/2009 | Johnson et al. | |
| 2009/0143403 | A1 | 6/2009 | Brown | |
| 2009/0286805 | A1 * | 11/2009 | Otoda et al. | 514/254.02 |
| 2010/0266696 | A1 | 10/2010 | Muhrer et al. | |

FOREIGN PATENT DOCUMENTS

| CN | 1832946 A | 9/2006 |
|---|---|---|
| EP | 1 884 242 A1 | 2/2008 |
| JP | 2003-160583 A | 6/2003 |
| WO | WO 99/16313 | 4/1999 |
| WO | WO 99/25354 | 5/1999 |
| WO | WO 00/18408 | 4/2000 |
| WO | WO 02/078673 A1 | 10/2002 |
| WO | WO 2005/016262 A2 | 2/2005 |
| WO | WO 2005/041970 A1 | 5/2005 |
| WO | WO 2006/055603 A2 | 5/2006 |
| WO | WO 2006/109183 A1 | 10/2006 |
| WO | WO 2007/035348 A2 | 3/2007 |

OTHER PUBLICATIONS

Horioka, Masayoshi, Chuushazai—sono kiso to chouzai to tekiyou—Kabushiki Kaisha Nanzandou, 1995, ISBN 4-525-77551-3, pp. 23-25.
Okano, Sadasuke, Sin Yakuzaigaku Souron ($3^{rd}$ revised edition). Kabushiki Kaisha Nankoudou, 1987, ISBN 4-524-49209-7, pp. 76-81.
Notification of Transmittal of Translation of the International Preliminary Report on Patentability, International Preliminary Report on Patentability, and Translation of the Written Opinion of the International Searching Authority, for International Patent Application No. PCT/JP2011/074375, mailed May 2, 2013 (7 pages).
International Search Report for Corresponding International Application No. PCT/JP2011/074375 mailed Jan. 24, 2012.
"Crysatiline Form of (3AR, 4S, 7R; 7AS)-2-[(1R, 2R)-2-[4-(1,2-Benzisothiazol-3-Yl)-Piperazin-1-Ylmethyl]-Cyclohexylmethyl] Hexahydro-4,7-Methano-2Hisoindole-1,3-Dione", IP.com Journal, IP.Com Inc., West Henrietta, NY, US, Mar. 28, 2011.
Hong, Yi et al., "Several Varieties of Injections State with Surfactants's Quality Specification and Safety", Chinese Journal of Experimental Traditional Medical Formulate, vol. 16, No. 1, pp. 115-119, 2010.
Rabinow, Barrett E., "Nanosuspension for Injection Administration," in "Nanoparticulate Drug Delivery Systems", Thassu, Deepak et al. Eds., Peking University Medical Press, pp. 35-41, Sep. 2010.

* cited by examiner

*Primary Examiner* — Tigabu Kassa
(74) *Attorney, Agent, or Firm* — Finnegan, Henderson, Farabow, Garrett & Dunner, L.L.P.

(57) ABSTRACT

The present invention relates to a composition comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof. In detail, the composition relates to a sustained release formulation for injection which maintains an effective blood level of the above-mentioned compound.

44 Claims, 5 Drawing Sheets

SUSTAINED-RELEASE FORMULATION FOR INJECTION

CROSS REFERENCE TO RELATED APPLICATION

This application claims the benefit of U.S. Provisional Application No. 61/394,069, filed Oct. 18, 2010, the content of which is incorporated herein by reference.

TECHNICAL FIELD

The present invention relates to a composition comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof (hereinafter, optionally referred to as "the present compound"). To be more specific, the present invention relates to a sterile suspension formulation which can maintain an effective blood level of the present compound as a sustained release formulation for injection. Furthermore, the present invention relates to a process of the formulation comprising the present compound.

BACKGROUND ART

It is known that N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide hydrochloride (hereinafter, optionally referred to as "Compound 1") has psychotropic activity and is useful as a therapeutic agent for diseases such as schizophrenia. Patent Reference 1 describes that Compound 1 is usually administered orally.

It is known that risperidone, olanzapine, aripiprazole, etc. have been already used in clinical practice as an agent for treating schizophrenia or other similar diseases. In order to promote patient compliance and reduce the relapse rate of schizophrenia, these medicaments for treating schizophrenia are desired to be modified to exert a long-term effect through a single administration.

A depot formulation for intramuscular injection comprising an injectable suspension of a medicament is generally known as one of administration means for sustained-release of a medicament. An injectable suspension is in a heterogeneous system comprising a solid phase dispersed in an aqueous or nonaqueous liquid phase, which requires sterile, stable, resuspendable, syringeable, injectable, isotonic, and nonirritating. In order to develop such depot formulation, in particular, it is necessary at least that such formulation is an aqueous one and additionally has satisfactory properties for an injectable suspension such as uniformity of dispersed particles of an active ingredient, sedimentation property of dispersed particles after still standing, re-suspensibility, and permeability in a needle (hereinafter, optionally referred to as "suspensibility"). In order to satisfy these requirements, for example, Patent Reference 2 discloses a composition comprising microparticles comprising a polymeric binder, and an aqueous injectable vehicle. The composition has a constructional property wherein the microparticles have a mass median diameter of at least about 10 µm, and the vehicle comprises a viscosity enhancing agent.

However, many of medicaments for treating schizophrenia or other similar diseases are hardly water-soluble, thus it is not easy to develop such formulation thereof which can make these requirements satisfied.

For example, a formulation comprising aripiprazole makes such requirements satisfied by reducing the mean particle size of the compound and adding a specific suspending agent such as carboxymethylcellulose thereto (Patent Reference 3). And, a formulation comprising olanzapine makes such requirements satisfied by further reducing the size of the compound to nanoparticles and using a surface stabilizer such as polysorbate (Patent Reference 4). As just described, in order to prepare a suspension comprising such hardly water-soluble compound, it is necessary to select an adaptable means in response to the property of the active ingredient after studying various means to meet the requirements.

To prepare a formulation for injection, some extra processes such as sterilization and dust free in a clean room are also required. In particular, a process under aseptic atmosphere is generally accompanied with some complicated and troublesome steps and manufacturing-operations. In addition, to comply with the predetermined level for assurance of aseptic preparation, some strict controls such as sterilization of apparatuses and devices, education and training for operators, and control of the number of environmental microbials and microparticles in an aseptic plant are also required.

PRIOR ART

Patent Reference

[Patent Reference 1] JP Patent No. 2800953
[Patent Reference 2] JP 2003-534366 T
[Patent Reference 3] JP 2007-509148 T
[Patent Reference 4] JP 2008-520581 T

DISCLOSURE OF INVENTION

Problem to be Solved by the Invention

Taking these conventional/current techniques into consideration, the present inventors attempted to improve the drug delivery property of Compound 1 as a medicament for treating schizophrenia or other similar diseases and tried finding an injectable suspension formulation which would satisfy the desired suspensibility. Compound 1 has a low solubility in water, and exhibits poor water solubility and hydrophobicity. This means that it is technically difficult to formulate the compound as an injectable product. To be more specific, when Compound 1 is dispersed in water, the particles thereof tend to come up to the surface or adhere to the container wall, and thus it was difficult to satisfy the suspensibility as an injectable suspension product. As a general technique to prepare an injectable suspension product with a sustained release property, Patent Reference 4 teaches that the releasing time can be adjusted by optimally controlling the particle size and it is preferred to keep the mean particle size of an active ingredient as small as possible. As for Compound 1, however, when the mean particle size thereof was too small, the sustained release for a long period could not be attained; whereas when the particles of bigger mean particle size were used so that the sustained release for a long period could be attained, then an injection needle was clogged with the particles, thus it was found that such bigger particles was difficult for be injected.

A problem to be solved by the invention is to provide a formulation that can maintain an effective blood level of the present compound for a long period (hereinafter, optionally referred to as "the present formulation"). In addition, the invention is intended to provide a process to accurately control the particle size of the present compound (hereinafter, optionally referred to as "the present process"). Furthermore, the invention is intended to provide a sterile and dust-free suspension formulation which can be easily processed without using complicated dosage forms and/or complicated processes.

(Means to Solve the Problem)

The present inventors have extensively studied to reach the above object and have surprisingly found that the above-mentioned problems could be solved by using a specific mean particle size of the present compound, a specific nonionic surfactant, and an active ingredient having an optimized concentration. The prepared suspension formulation for injection thereby exhibits a good suspensibility and is able to pass through an injection needle easily. Based upon the new findings, the present invention has been completed.

The present inventions are as follows:

Term 1

A composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection.

Term 2

The composition of Term 1 wherein the active ingredient is in a crystal form.

Term 3

The composition of Term 2 wherein the mean particle size of the crystal is about 4 μm-about 55 μm, about 4 μm-about 26 μm, about 4 μm-about 20 μm, about 4 μm-about 18 μm, about 4 μm-about 16 μm, about 5 μm-about 55 μm, about 5 μm-about 26 μm, about 5 μm-about 20 μm, about 5 μm-about 18 μm, about 5 μm-about 16 μm, about 8 μm-about 55 μm, about 8 μm-about 20 μm, about 10 μm-about 55 μm, about 10 μm-about 26 μm, about 10 μm-about 20 μm, about 10 μm-about 18 μm, or about 10 μm-about 16 μm.

Term 4

The composition of Term 3 wherein the mean particle size of the crystal is about 5 μm-about 55 μm.

Term 5

The composition of Term 3 wherein the mean particle size of the crystal is about 5 μm-about 26 μm.

Term 6

The composition of Term 3 wherein the mean particle size of the crystal is about 5 μm-about 20 μm.

Term 7

The composition of Term 3 wherein the mean particle size of the crystal is about 5 μm-about 16 μm.

Term 8

The composition of Term 3 wherein the mean particle size of the crystal is about 10 μm-about 20 μm.

Term 9

The composition of Term 3 wherein the mean particle size of the crystal is about 10 μm-about 16 μm.

Term 10

The composition of any one of Terms 2 to 9 wherein the crystal is a cubic crystal.

Term 11

The composition of Term 10 wherein the ratio between length and width of the cubic crystal is about 1:1, and the ratio between length and height thereof is about 1:0.8 to about 1:1.2.

Term 12

The composition of any one of Term 2 to 11 wherein the active ingredient in crystal form is contained in about 5% (w/v) to about 60% (w/v) per the whole of the composition.

Term 13

The composition of any one of Terms 1 to 12 wherein the surfactant is polysorbate 80.

Term 14

The composition of any one of Terms 1 to 13 wherein the surfactant is contained in about 0.005% (w/v) to about 2% (w/v) per the whole of the composition.

Term 15

The composition of any one of Terms 1 to 14 wherein the buffer is at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid.

Term 16

The composition of Term 15 wherein the buffer is sodium dihydrogenphosphate and/or disodium hydrogen-phosphate.

Term 17

The composition of any one of Terms 1 to 16 wherein the buffer is contained in about 0.01% (w/v) to about 2% (w/v) per the whole of the composition.

Term 18

The composition of any one of Terms 1 to 17 wherein the isotonic agent is sodium chloride.

Term 19

The composition of any one of Terms 1 to 18 wherein the isotonic agent is contained in about 0.1% (w/v) to about 10% (w/v) per the whole of the composition.

Term 20

A sustained release formulation for injection which comprises the composition according to any one of Terms 1 to 19.

Term 21

The formulation of Term 20 wherein the active ingredient is contained in a concentration of about 50 mg/mL to about 600 mg/mL.

Term 22

The formulation of Term 21 wherein the active ingredient is contained in a concentration of about 50 mg/mL to about 400 mg/mL.

Term 23

The formulation of Term 22 wherein the active ingredient is contained in a concentration of about 100 mg/mL to about 400 mg/mL.

Term 24

The formulation of Term 23 wherein the active ingredient is contained in a concentration of about 100 mg/mL to about 200 mg/mL.

Term 25
The formulation of Term 23 wherein the active ingredient is contained in a concentration of about 200 mg/mL to about 400 mg/mL.

Term 26
The formulation of any one of terms 20 to 25 wherein the surfactant is contained in a concentration of about 0.05 mg/mL to about 20 mg/mL.

Term 27
The formulation of any one of Terms 20 to 26 wherein the buffer is contained in a concentration of about 0.1 mg/mL to about 20 mg/mL.

Term 28
The formulation of any one of Terms 20 to 27 wherein the isotonic agent is contained in a concentration of about 1 mg/mL to about 100 mg/mL.

Term 29
The formulation of any one of Terms 20 to 28 which contains about 50 mg to about 1200 mg of the active ingredient per a container.

Term 30
The formulation of Term 29 which contains about 100 mg to about 800 mg of the active ingredient per a container.

Term 31
The formulation of any one of Terms 20 to 30 which can pass through a needle of 18 to 23 gauges.

Term 32
The formulation of any one of Terms 20 to 31 wherein the sustained release formulation for injection is a depot formulation for injection.

Term 33
A process of a sustained-release sterile formulation for injection comprising the following steps (1) to (5):
step (1): dissolving a mixture comprising N-[4-[4-(1,2-benzisothiazol-3-yl)-1-piperazinyl]-(2R,3R)-2,3-tetra-methylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water, and then sterilely-filtering the solution,
step (2): preparing a water solution comprising a surfactant and a buffer, sterilely filtering the water solution, and then sterilely putting the water solution into a sealed vessel whose inside is sterilized,
step (3): sterilely adding the sterile solution prepared in step (1) into the sealed vessel containing the water solution prepared in step (2),
step (4): collecting a crystal precipitated in step (3) through a filter in the sealed vessel, and
step (5): preparing a water solution comprising a surfactant, a buffer, an isotonic agent and water for injection, sterilely filtering the water solution, and then sterilely putting the water solution into the sealed vessel containing the crystal in step (4) and mixing the water solution and the crystal.

Term 34
A process of a sustained-release formulation for injection comprising the following steps (1) to (5):
step (1): dissolving a mixture comprising N-[4-[4-(1,2-benzisothiazol-3-yl)-1-piperazinyl]-(2R,3R)-2,3-tetra-methylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient,
step (2): preparing a water solution comprising a surfactant and a buffer (i.e. a crystallizing agent),
step (3): adding the solution of the active ingredient prepared in step (1) into the crystallizing agent in step (2),
step (4): collecting a crystal precipitated in step (3) through a filter, and
step (5): preparing a water solution comprising a surfactant, a buffer, an isotonic agent and water for injection (i.e. a vehicle solution), and then mixing the water solution and the crystal of the active ingredient prepared in step (4) to prepare a suspension formulation.

Term 35
A process of a sustained-release formulation for injection comprising the following steps (1) to (5):
step (1): dissolving a mixture comprising N-[4-[4-(1,2-benzisothiazol-3-yl)-1-piperazinyl]-(2R,3R)-2,3-tetra-methylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient,
step (2): preparing a water solution comprising a surfactant and a buffer (i.e. a crystallizing agent), and then injecting the water solution into a vessel for crystallization,
step (3): adding the solution of the active ingredient prepared in step (1) into the vessel for crystallization containing the crystallizing agent in step (2),
step (4): collecting a crystal precipitated in step (3) through a filter in the vessel for crystallization, and
step (5): preparing a water solution comprising a surfactant, a buffer, an isotonic agent and water for injection (i.e. a vehicle solution), and then injecting the water solution into the crystal of the active ingredient prepared in step (4) and mixing the water solution and the crystal to prepare a suspension formulation.

Term 36
The process of any one of Terms 33 to 35 further followed by the following steps (6) to (8):
step (6): aseptically filling a formulation container with the suspension formulation prepared in step (5) to prepare a filled suspension formulation,
step (7): sterilizing the filled suspension formulation prepared in step (6) by a process of steaming under pressure, and
step (8): ultrasonicating the filled suspension formulation prepared in step (7).

Term 37
The process of Term 36 wherein the formulation container is a prefilled syringe or a vial.

Term 38
The process of Term 36 or 37 wherein the temperature of the steam sterilization under pressure is 100 to 150° C.

Term 39
The process of any one of Terms 33 to 38, in step (3) the solution of the active ingredient is added to the crystallizing agent in the vessel for crystallization (or the sealed vessel) while circulating the solution (or the suspension solution) in the vessel for crystallization (or the sealed vessel) via a bypass pathway equipped with a pump which can pressure a solution.

Term 40
The process of any one of Term 39 wherein the pump in the bypass pathway is any one pump selected from a roller pump (tube pump, hose pump), a reciprocating pump (piston pump, plunger pump, diaphragm pump), and a rotary pump (gear pump, vane pump, screw pump).

Term 41
The process of Term 39 wherein the pump in the bypass pathway is a roller pump.

Term 42
The process of any one of Terms 39 to 41 wherein the circulation velocity of the bypass pathway is about 0.001 to about 2 parts by volume/min per one part of the total volume of the crystallizing agent and the solution of the active ingredient.

Term 43
The process of any one of Terms 39 to 41 wherein the circulation velocity of the bypass pathway is about 0.01 to about 1 parts by volume/min per one part of the total volume of the crystallizing agent and the solution of the active ingredient.

Term 44
A process of a sustained-release formulation for injection comprising the following steps (1) to (5):
step (1): dissolving a mixture comprising N-[4-[4-(1,2-benzisothiazol-3-yl)-1-piperazinyl]-(2R,3R)-2,3-tetra-methylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an, organic solvent and water to prepare a solution of the active ingredient,
step (2): preparing a water solution comprising a surfactant and a buffer (i.e. a crystallizing agent) and injecting the water solution into a vessel for crystallization equipped with a stirring system,
step (3): adding the solution of the active ingredient to the crystallizing agent in the vessel for crystallization while circulating the solution (or the suspension solution) in the vessel for crystallization via a bypass pathway equipped with a pump which (i) is connected to the vessel for crystallization, (ii) can make the solution in the vessel for crystallization circulated, and (iii) can pressure the solution,
step (4): collecting a crystal precipitated in the vessel for crystallization from the solution (or the suspension solution) in step (3) through a filter, and
step (5): preparing a water solution comprising a surfactant, a buffer, an isotonic agent and water for injection (i.e. a vehicle solution), and then injecting the water solution into the crystal of the active ingredient prepared in step (4) and mixing them to prepare a suspension formulation.

Term 45
A process of a sustained-release formulation for injection comprising the following steps (4) to (8):
step (4): preparing a vehicle solution comprising a surfactant, a buffer, an isotonic agent and water for injection,
step (5): injecting the vehicle solution in step (4) into a crystal of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide and mixing them to prepare a suspension formulation,
step (6): aseptically filling a formulation container with the suspension formulation prepared in step (5) to prepare a filled suspension formulation
step (7): sterilizing the filled suspension formulation prepared in step (6) by a process of steaming under pressure, and
step (8): ultrasonicating the filled suspension formulation prepared in step (7).

Term 46
The process of any one of Terms 33 to 45 wherein each the surfactant is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate.

Term 47
The process of any one of Terms 33 to 46 wherein the organic solvent is at least one solvent selected from the group consisting of 1-propanol, methanol, ethanol, 2-propanol, acetone, dimethylsulfoxide and N,N-dimethylacetamide.

Term 48
The process of any one of Terms 33 to 47 wherein the solvent used in step (1) is a mixture of an organic solvent and water.

Term 49
The process of Term 48 wherein the mixture solvent is a water-containing alcohol.

Term 50
The process of Term 49 wherein the content of alcohol in the water-containing alcohol is 40% to 90%.

Term 51
The process of Term 49 wherein the content of alcohol in the water-containing alcohol is 50% to 90%.

Term 52
The process of any one of Terms 33 to 51 wherein the alcohol is ethanol.

Term 53
The process of any one of Terms 33 to 52 wherein each the buffer is independently at least one ingredient selected from the group consisting of sodium dihydrogenphosphate, disodium hydrogenphosphate, potassium dihydrogenphosphate, dipotassium hydrogenphosphate, sodium carbonate, triethanolamine, arginine and meglumine.

Term 54
The process of any one of Terms 33 to 53 wherein the isotonic agent is sodium chloride and/or D-mannitol.

Term 55
A sustained release formulation for injection which is prepared through the process of any one of Terms 33 to 54.

Term 56
A crystal of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide whose mean particle size is in a range selected from the group consisting of about 4 μm-about 55 μm, about 4 μm-about 26 μm, about 4 μm-about 20 μm, about 4 μm-about 18 μm, about 4 μm-about 16 μm, about 5 μm-about 55 μm, about 5 μm-about 26 μm, about 5 μm-about 20 μm, about 5 μm-about 18 μm, about 5 μm-about 16 μm, about 8 μm-about 55 μm, about 8 μm-about 20 μm, about 10 μm-about 55 μm, about 10 μm-about 26 μm, about 10 μm-about 20 μm, about 10 μm-about 18 μm, and about 10 μm-about 16 μm.

Term 57
The crystal of Term 56 wherein the mean particle size of the crystal is about 5 μm-about 55 μm.

Term 58
The crystal of Term 56 wherein the mean particle size of the crystal is about 5 μm-about 26 μm.

Term 59
The crystal of Term 56 wherein the mean particle size of the crystal is about 5 μm-about 20 μm.

Term 60
The crystal of Term 56 wherein the mean particle size of the crystal is about 5 μm-about 16 μm.

Term 61
The crystal of Term 56 wherein the mean particle size of the crystal is about 10 μm-about 20 μm.

Term 62
The crystal of Term 56 wherein the mean particle size of the crystal is about 10 μm-about 16 μm.

Term 63

A crystal of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide (free form of Compound 1) which has a powder X-ray diffraction pattern showing diffraction angle 2θ (°) of 15.1±0.2, 15.5±0.2, 16.3±0.2, 16.6±0.2, 18.0±0.2, and 20.0±0.2.

Term 64

A crystal of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide (free form of Compound 1) which has a powder X-ray diffraction pattern showing diffraction angle 2θ (°) of 11.2±0.2, 15.1±0.2, 15.5±0.2, 16.3±0.2, 16.6±0.2, 18.0±0.2, 19.1±0.2, 19.5±0.2, 20.0±0.2, 20.9±0.2, 22.3±0.2, and 26.0±0.2.

Term 65

The crystal of any one of Terms 56 to 62 which has a powder X-ray diffraction pattern showing diffraction angle 2θ (°) of 15.1±0.2, 15.5±0.2, 16.3±0.2, 16.6±0.2, 18.0±0.2, and 20.0±0.2.

Term 66

The crystal of any one of Terms 56 to 65 wherein the crystal is a cubic crystal.

Term 67

The crystal of Term 66 which is a cubic crystal wherein the ratio between length and width of the cubic crystal is about 1:0.8 to about 1:1.2, and the ratio between length and height thereof is about 1:0.1 to about 1:3.

Term 68

A depot formulation for injection comprising the crystal of any one of Terms 56 to 67.

Term 69

The depot formulation for injection of Term 68 wherein the crystal is suspended in a medium of the formulation.

Term 70

The depot formulation for injection of Term 69 wherein the medium is water.

Term 71

The depot formulation for injection of any one of Terms 68 to 70 which further comprises a surfactant, a buffer and an isotonic agent.

Term 72

A package containing a container which contains the sustained release formulation for injection comprising the crystal of any one of Terms 56 to 67.

Term 73

A method for treating psychiatric disease which comprises administering the formulation of any one of Terms 20 to 32, 55, and 68 to 71.

Term 74

The method of Term 73 wherein the psychiatric disease is schizophrenia.

Term 75

The method of Term 73 wherein the psychiatric disease is bipolar disorder.

Term 76

The method of Term 73 wherein the psychiatric disease is depression.

Effect of the Invention

The present formulation can maintain an effective blood level of the present compound for at least 2 to 4 weeks or more by intramuscular administration. Consequently, using the present formulation, it is possible to decrease the frequency of administration compared with an oral formulation containing the present compound. The present formulation is injectable (i.e. has a good needle passability) even though the present compound is suspended in the present formulation. The present process provides the formulation to maintain an effective blood level of the present compound for at least 2 to 4 weeks or more by suspending the present compound in the formulation. In addition, the present process is useful in the point that the preparation is carried out under a sequential sterile and/or dust-free processing, further via a continuous formulating process.

BEST MODE FOR CARRYING OUT THE INVENTION

Figure 1:
FIG. 1 shows a photomicrograph of the crystal of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide.

The term "active ingredient" used herein is N-[4-[4-(1,2-benzisothiazol-3-yl)-1-piperazinyl]-(2R,3R)-2,3-tetra-methylene-butyl]-(1'R,2'S,3'R,4'S)-2,3-bicyclo[2,2,1]-heptanedicarboximide or a pharmaceutically acceptable acid addition salt thereof. Preferably, the term refers to N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a hydrochloride thereof. The concentration of the active ingredient used herein is within about 5% (w/v) to about 60% (w/v) per the whole of the formulation as a free form.

In addition, the concentration of the active ingredient in the formulation is preferably about 50 mg/mL to about 600 mg/mL as a free form, and more preferably about 50 mg/mL to about 400 mg/mL, about 100 mg/mL to about 400 mg/mL, about 100 mg/mL to about 200 mg/mL, or about 200 mg/mL to about 400 mg/mL as a free form.

The "particle size" is controlled to maintain an effective blood level of the active ingredient for at least two weeks, preferably for at least four weeks. The mean particle size of the "active ingredient" used herein is in a range selected from the group consisting of about 4 μm-about 55 μm, about 4 μm-about 26 μm, about 4 μm-about 20 μm, about 4 μm-about 18 μm, about 4 μm-about 16 μm, about 5 μm-about 55 μm, about 5 μm-about 26 μm, about 5 μm-about 20 μm, about 5 μm-about 18 μm, about 5 μm-about 16 μm, about 8 μm-about 55 μm, about 8 μm-about 20 μm, about 10 μm-about 55 μm, about 10 μm-about 26 μm, about 10

μm-about 20 μm, about 10 μm-about 18 μm, and about 10 μm-about 16 μm. Preferably, the mean particle size is about 5 μm-about 5.5 μm, about 5 μm-about 26 μm, about 5 μm-about 20 μm, about 5 μm-about 16 μm, about 10 μm-about 20 μm, or about 10 μm-about 16 μm. The term "mean particle size (also referred to as D50)" used herein is defined as a median diameter based on the volume, which was obtained by measuring the particle size distribution through a wet process with a laser diffraction particle size distribution analyzer.

The term "pharmaceutically acceptable acid addition salt" used herein is defined as an addition salt with an inorganic acid or an organic acid. The inorganic acid includes, for example, hydrochloric acid, hydrobromic acid, hydroiodic acid, and sulfuric acid. The organic acid includes, for example, phosphoric acid, acetic acid, oxalic acid, citric acid, malic acid, tartaric acid, maleic acid, and fumaric acid. Preferably, the salt is hydrochloride.

The "surfactant" is used to improve the suspensibility of the crystal in the present formulation, and is contained in a range of about 0.005 to about 2% (w/v) per the whole of the formulation, preferably about 0.01 to about 1% (w/v). In addition, the surfactant is contained in a concentration of about 0.05 mg/mL to about 20 mg/mL. The surfactant includes, for example, polysorbate 80, polysorbate 20, polyoxyethylene hydrogenated castor oil 50, polyoxyethylene hydrogenated castor oil 60, poloxamer 188, and polyoxyethylene castor oil. Preferably, the surfactant is polysorbate 80. In addition, the present invention may contain more than two surfactants.

The "buffer" is used in an appropriate amount to adjust the pH of the aqueous suspension in the present formulation to an injectable range, for example about pH 6 to about pH 8 and preferably about pH 7. The buffer is contained in a range of about 0.01 to about 2% (w/v) per the whole of the formulation, and preferably about 0.05 to about 1% (w/v). In addition, the buffer is contained in a concentration of about 0.1 mg/mL to about 20 mg/mL. The buffer includes, for example, sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine, and citric acid. Preferably, the buffer is sodium phosphate. In addition, the present invention may contain more than two buffers.

The "isotonic agent" is used to adjust the osmotic pressure of the present formulation to an injectable range. The isotonic agent is contained in a range of about 0.1 to 10% (w/v) per the whole of the formulation, preferably about 0.2 to about 5% (w/v). In addition, the isotonic agent is contained in a concentration of about 1 mg/mL to about 100 mg/mL. The isotonic agent includes, for example, sodium chloride, and D-mannitol. Preferably, the isotonic agent is sodium chloride.

The term "water" used herein is defined as purified water, or the same or a higher grade thereof; and such water needs to be sterilized after dissolving various ingredients therein, or already-sterilized water (e.g. water for injection) is used in the process which is carried out under sterile condition throughout the steps. In addition, the term "water for injection" used herein includes water sterilized through a sterile filter etc. after dissolving substrates or reagents into the above-mentioned "water" (as a starting material).

As shown in FIG. 1, the crystal of N-[4-[4-(1,2-benzisothiazol-3-yl)-1-piperazinyl]-(2R,3R)-2,3-tetra-methylenebutyl]-(1'R,2'S,3'R,4'S)-2,3-bicyclo[2,2,1]-heptanedicarboximide or a pharmaceutically acceptable acid addition salt thereof is characterized by a cubic crystal form just after being prepared through the present process. And then, the crystal might be gradually rounded and transformed into a spherical form during storage. In addition, the cubic crystal used herein includes not only perfect cubic shapes but also cuboidal shapes (e.g. shapes whose ratio between length and width is about 1:0.8 to about 1:1.2, and the ratio between length and height thereof is about 1:0.1 to about 1:3, etc.).

The "sustained release formulation for injection" used herein means a formulation which can maintain the blood level of the active ingredient for at least two to four weeks after intramuscular injection.

The present formulation may contain other additive agents unless there are any adverse effects on the present invention. The other additive agents includes, for example, pH regulators such as hydrochloric acid, acetic acid, lactic acid, sulfuric acid, phosphoric acid, methanesulfonic acid, tartaric acid, and sodium hydroxide; soothing agents such as lidocaine hydrochloride, meprylcaine hydrochloride and procaine hydrochloride; water-soluble polymers such as carboxymethylcellulose sodium, hydroxypropylcellulose, hydroxypropyl methyl-cellulose, hydroxymethylcellulose, methylcellulose, polyvinylpyrrolidone, polyvinyl alcohol, polyethylene glycol 4000, carboxy vinyl polymer, polypeptide, polyamino acid, dextrin, gum arabic, sodium alginate, pullulan, sodium hyaluronate, sodium chondroitin sulfate, gelatin, collagen, agarose, xanthane gum, gellan gum, tamarind gum, guar gum, carrageenan, locust bean gum, karaya gum, tragacanth gum, tara gum, psyllium seed gum, ghatti gum, curdlan, and pectin; and other polymers such as sulfobutylether β-cyclodextrin, hydroxypropyl β-cyclodextrin, polylysine, polyglutamic acid, chitin, chitosan, polylactic acid, polyglycolic acid and sucrose acetate isobutylate.

The present formulation can be administered parenterally, in particular, intramuscularly or subcutaneously as a sustained release formulation for injection, at a dose of 50 to 1200 mg (preferably 100 to 800 mg) of the active ingredient. The present formulation can be administered once in two to six weeks, preferably once in four to six weeks, and more preferably once in four weeks.

The present formulation may contain 50 to 1200 mg of the active ingredient per a bottle, and preferably 100 to 800 mg thereof.

The present formulation can be administered intramuscularly or subcutaneously with a prefilled syringe equipped with a needle which is filled with the present formulation. Alternatively, the present formulation can be administered through the following steps; i.e., from a vial filled with the present formulation, the content is transferred into an injection syringe via a needle and then administered intramuscularly or subcutaneously. Furthermore, the present formulation may be put into a container such as a vial and then lyophilized to give a lyophilize formulation, or the crystal of the active ingredient in the present formulation may be isolated, dried, and then put into a container such as a vial to give a powder-filled formulation. The lyophilize formulation or the powder-filled formulation can be administered intramuscularly or subcutaneously as an injectable suspension which is prepared by putting a suspending solution into the container via a needle just before use. A needle of 18 gauge (internal diameter thereof: 0.90 mm) to 23 gauge (internal diameter thereof: 0.33 mm) may be used for the intramuscular or subcutaneous administration. Furthermore, the container filled with the formulation of the present invention can be set in a needleless syringe which can administer a drug solution in the container by discharging the solution with a pressure prepared by a gas, a detonator, a spring, etc. packed in the syringe device without using any needle to administer the drug solution intramuscularly or subcutaneously. The formulation of the present invention includes a form of liquid such as a suspension which can be put in a formulation container, a form wherein the liquid such as a suspension is already put in a formulation container, and further a form wherein the formulation container containing the liquid is sterilized and/or ultrasonicated.

The present formulation can be prepared according to, for example, the following steps, but are not limited thereto.

Preparation Method A:

Step (1):

The present compound is dissolved in water, an organic solvent or a mixture thereof with a surfactant to prepare a solution of the active ingredient. The resulting solution is sterilely filtered through a sterile filter to prepare a sterile solution of the active ingredient. The solvent used herein (water, an organic solvent or a mixture thereof) is preferably an organic solvent or a mixture of an organic solvent and water, more preferably a mixture of an organic solvent and water. Sterile filters are effective not only for sterilely-filtering, but also for removing foreign substances derived from starting materials or foreign substances immixed as a contamination during processing steps. The surfactant includes, for example, polysorbate 80, polysorbate 20, polyoxyethylene hydrogenated castor oil 50, polyoxyethylene hydrogenated castor oil 60, poloxamer 188, polyoxyethylene castor oil, benzalkonium chloride, and sodium lauryl sulfate. In addition, two or more of the surfactants may be used. Preferably, the surfactant is polysorbate 80. Preferably, the surfactant is contained in about 0.005% (w/v) to about 10% (w/v).

The water used herein is purified water or the same or high level of water, or water for injection.

The organic solvent includes, for example, alcohol solvents (e.g. methanol, ethanol, etc.), and aprotic solvents (e.g. acetone, dimethylsulfoxide, N,N-dimethylacetamide, etc.). In addition, two or more of the solvents may be used. Preferably, the organic solvent is 1-propanol, methanol, ethanol, 2-propanol, acetone, dimethylsulfoxide, or N,N-dimethylacetamide.

The term "mixture of an organic solvent and water" is defined as a mixed solvent comprising the above-mentioned alcohol solvent and/or the above-mentioned aprotic solvent and water (hereinafter, the mixture of an alcohol solvent and water is optionally referred to as "water-containing alcohol solvent"). The mixture of an organic solvent and water includes, for example, a mixture of 1-propanol, methanol, ethanol, 2-propanol, acetone, dimethylsulfoxide, or N,N-dimethylacetamide, and water. The preferable mixture is a mixture of ethanol and water (optionally referred to as "water-containing ethanol").

The organic solvent in the mixture of an organic solvent and water may be contained in the range of 0% to 100% as long as the organic solvent and water can be homogeneously mixed, for example, in 30% to 95%, preferably 40% to 90%, more preferably 50% to 90%, and even more preferably 60% to 80%. It is especially preferred that the mixture is 70% water-containing ethanol. Preferably, the organic solvent is contained in about 50 to about 90% per the whole volume of the composition. The temperature in this step is about 1 to about 90° C., preferably about 5 to about 60° C.

Step (2):

A water solution comprising a surfactant and a buffer is prepared to give a crystallizing agent. The water solution (crystallizing agent) is sterilely filtered through a sterile filter to give a sterile crystallizing agent, and then the agent is sterilely put into a vessel for crystallization whose inside is sterilized (hereinafter, optionally referred to as a "sealed-type vessel for crystalline" or a "sealed vessel").

The surfactant includes, for example, polysorbate 80, polysorbate 20, polyoxyethylene hydrogenated castor oil 50, polyoxyethylene hydrogenated castor oil 60, poloxamer 188, polyoxyethylene castor oil, benzalkonium chloride, and sodium lauryl sulfate. Two or more of the surfactants may be used. The surfactant may be added to the water solution (i.e. crystallizing agent) and/or the sterile solution prepared in step (1) (i.e. sterile solution of the active ingredient). Preferably, the surfactant is polysorbate 80. Preferably, the surfactant is contained in about 0.005% (w/v) to about 10% (w/v). The buffer includes, for example, sodium phosphate, sodium dihydrogenphosphate, disodium hydrogenphosphate, potassium dihydrogenphosphate, dipotassium hydrogenphosphate, sodium carbonate, triethanolamine, arginine, and meglumine. Two or more of the buffers may be used. Preferably, the buffer is sodium dihydrogenphosphate or disodium hydrogenphosphate. Preferably, the buffer is contained in about 0.01% (w/v) to about 8% (w/v). The pH of the water solution is about 5 to about 12, and preferably about 7 to about 10. The temperature in this step is about 1 to about 90° C., and preferably about 5 to about 80° C.

The sealed vessel used in this step includes, for example, a vessel made of stainless (e.g. SUS304, SUS316, SUS316L) which is equipped with pipe arrangement, ferrule, valve, jacket, air filter, stirring system, etc. The stirring system includes, for example, a part of any stirring system selected from stirring wings (e.g. paddle wings, turbine wings, propeller wings, Pfaudler wings, bar wings, anchor wings), a homomixer, a static mixer and a stirring bar for a magnetic stirrer.

Step (3): Process of Crystallization

The sterile solution prepared in step (1) (sterile solution of the active ingredient) is sterilely dropped into the vessel for crystallization (sealed vessel) containing the water solution prepared in step (2) (crystallizing agent). The volume ratio between the solutions of step (2) and step (1) (i.e. volume ratio between the crystallizing agent and the solution of the active ingredient) is about 1:0.1 to about 1:10, preferably about 1:0.2 to about 1:2.

The present compound is crystallized in this step. The precipitated crystal is a cubic crystal wherein the ratio between length and width of the cubic crystal is about 1:1, and the ratio between length and height thereof is about 1:0.8 to about 1:1.2. The mean particle size of the crystal can be controlled by adjusting the crystallizing temperature, stirring speed, dropping rate, etc., or by adjusting the circulation velocity when using a bypass pathway mentioned below. The crystallizing temperature is preferably about 1 to about 90° C., and more preferably about 5 to about 60° C. The stirring speed is preferably about 50 rpm to about 10000 rpm, more preferably 100 rpm to about 5000 rpm, even more preferably about 100 rpm to about 2000 rpm, and the most preferably about 300 rpm to about 1500 rpm. The dropping rate is calculated by dividing the total volume of the sterile solution of step (1) (i.e. sterile solution of the active ingredient) to be added in Step (3) by the desired time. The dropping rate is, when the total dropped volume of the solution of the active ingredient is n L, preferably about n×0.01 L/min. to n×1 L/min, more preferably about n×0.01 L/min to about n×0.2 L/min, and even more preferably about n×0.05 L/min to about n×0.2 L/min. In more detail, for example, when the total dropped volume of the solution of the active ingredient is 1 L, the dropping rate is about 0.01 L/min to 1 L/min, preferably about 0.01 L/min to about 0.2

L/min, more preferably about 0.05 L/min to about 0.2 L/min; and when the total dropped volume of the solution of the active ingredient is 100 L, the dropping rate is about 1 L/min to 100 L/min, preferably about 1 L/min to about 20 L/min, more preferably about 5 L/min to about 20 L/min. And, when the total dropped volume of the solution of the active ingredient is 1000 L, the dropping rate is about 10 L/min to 1000 L/min, preferably about 10 L/min to about 200 L/min, more preferably about 50 L/min to about 200 L/min.

In the step (crystallizing step), the sterile solution (sterile solution of the active ingredient) prepared in step (1) can be sterilely added dropwise thereto and simultaneously circulating the solution in the vessel for crystallization via a sealed bypass pathway. Preferably, the bypass pathway has a pump which can pressure a solution in the pathway. Such pump which can pressure a solution includes, for example, a roller pump (tube pump, hose pump), a reciprocating pump (piston pump, plunger pump, diaphragm pump), and a rotary pump (gear pump, vane pump, screw pump), preferably a roller pump.

The circulation velocity in the bypass pathway is preferably about n×0.001 L/min to about n×2 L/min, more preferably about n×0.01 L/min to about n×1 L/min wherein "n" denotes the total volume of the crystallizing agent and the solution of the active ingredient. In more detail, the circulation velocity is about 1 mL/min to about 2000 mL/min, preferably about 10 mL/min to about 1000 mL/min when the total volume of the crystallizing agent and the solution of the active ingredient is 1 L; about 100 mL/min to about 200 L/min, preferably about 1 L/min to about 100 L/min when the total volume of the crystallizing agent and the solution of the active ingredient is 100 L; and about 1 L/min to about 2000 L/min, preferably about 10 L/min to about 1000 L/min when the total volume of the crystallizing agent and the solution of the active ingredient is 1000 L.

Step (4):

The crystal precipitated in step (3) is collected through a filter in the sealed vessel. The crystal produced under the condition of in step (3) such as crystallizing temperature and stirring speed has uniform mean particle sizes. The method therefore can prepare a crystal having uniform mean particle sizes without any milling steps. The sealed vessel used in this step includes, for example, a pressurized vessel made of stainless (e.g. SUS304, SUS316, SUS316L) which is equipped with pipe arrangement, ferrule, valve, crystal collection filter, jacket, air filter, stirring system, etc. The stirring system includes, for example, a part of any stirring system selected from stirring wings (e.g. paddle wings, turbine wings, propeller wings, Pfaudler wings, bar wings, anchor wings) and a stirring bar for a magnetic stirrer.

Step (5):

A water solution (vehicle solution) comprising a surfactant (about 0.005 to about 2% (w/v) per the whole of the final formulation), a buffer (about 0.01 to about 2% (w/v) per the whole of the final formulation), an isotonic agent (about 0.1 to about 10% (w/v) per the whole of the final formulation), and water for injection is prepared. The vehicle solution may further comprise a pH regulator, a soothing agent, a polymer, etc. The prepared solution is sterilely filtered through a sterile filter. The resulting vehicle solution is sterilely put into the sealed vessel of step (4) to wash the crystal in the vessel. The washing process may be repeated several times. After washing the crystal, the vehicle solution can be sterilely put into the sealed vessel again and mixed with the crystal to provide a suspension formulation which is the formulation of the invention. In addition, the sterile active ingredient prepared in step (4) may be continuously suspended in the vehicle solution to provide an injectable product (suspension formulation), and furthermore, the active ingredient obtained from the crystallization may be washed with water, an organic solvent or a mixture thereof any of which are sterilely filtered through a sterile filter, and then dried for a while and suspended in the vehicle solution again to prepare a suspension formulation.

The suspension formulation prepared in Step (5) can be formed as a prefilled formulation through the following step (6).

Step (6):

The suspension formulation prepared in Step (5) is sterilely put into a container for formulation such as a prefilled syringe, a vial, an ampule, a bag or a Blow-Fill-Seal container. The preferred container includes a prefilled syringe and a vial.

All of Steps (1) to (6) in the Preparation Method A mentioned above can be continuously carried out under sterile conditions without taking out the crystal during the process. According to the present process, it is possible to easily prepare a sustained release formulation for injection without using the steps of gas sterilization, gamma-ray sterilization, or electron beam sterilization, which is a sterile and dust-free formulation. In addition, the present process provides a sustained-release sterile formulation for injection wherein the active ingredient is uniformly suspended in the solvent.

Preparation Method B:

Preparation Method A can be partially modified as follows. In the following Preparation Method B, the suspension formulation prepared via Step (1) to Step (5) or Step (6) is not necessarily ensured about sterility. In the following Preparation Method B, the embodiments or preferable embodiments of a surfactant, water, an organic solvent, a mixed solvent of an organic solvent and water, a buffer, an isotonic agent, a bypass pathway, a formulation container, etc. used herein can be the same as Preparation Method A, unless otherwise indicated. In addition, pH, temperature, liquid volume ratio, stirring speed, dropping speed, circulation velocity, etc. used herein are also the same as Preparation Method A, unless otherwise indicated.

Step (1):

The present compound is dissolved in water, an organic solvent or a mixture thereof with a surfactant to prepare a solution of the active ingredient.

Step (2):

A water solution comprising a surfactant and a buffer is prepared to give a crystallizing agent. The crystallizing agent is injected into a vessel for crystallization.

The vessel for crystallization used herein is equipped with a stirring system, whose internal capacity is big enough to contain a solution of the active ingredient and the crystallizing agent. The material of the vessel for crystallization includes a stainless vessel (e.g. SUS304, SUS316, SUS316L). The stirring system set in the vessel for crystallization includes, for example, a part of any stirring system selected from stirring wings (e.g. paddle wings, turbine wings, propeller wings, Pfaudler wings, bar wings, anchor wings), a homomixer, a static mixer and a stirring bar for a magnetic stirrer.

Step (3): Process of Crystallization

The solution of the active ingredient prepared in step (1) is dropped into the vessel for crystallization containing the water solution prepared in step (2) (crystallizing agent). The volume ratio between the crystallizing agent and the solution of the active ingredient is about 1:0.1 to about 1:10, preferably about 1:0.2 to about 1:2.

The present compound is crystallized in this step. The precipitated crystal is a cubic crystal wherein the ratio between length and width of the cubic crystal is about 1:1, and the ratio between length and height thereof is about 1:0.8 to about 1:1.2. The mean particle size of the crystal can be controlled by adjusting the crystallizing temperature, stirring speed, dropping rate, etc., or by adjusting the circulation velocity when using the bypass pathway mentioned below.

In the step (crystallizing step), the solution of the active ingredient prepared in step (1) can be added dropwise thereto and simultaneously circulating the solution in the vessel for crystallization via a bypass pathway. Preferably, the bypass pathway has a pump which can pressure a solution in the pathway. Such pump which can pressure a solution includes, for example, a roller pump (tube pump, hose pump), a reciprocating pump (piston pump, plunger pump, diaphragm pump), and a rotary pump (gear pump, vane pump, screw pump), preferably a roller pump. Namely, one embodiment of the device which can be used in the crystallizing process of the present invention includes a device equipped with (1) a vessel for crystallization which has a stirring part and can contain a solution of the active ingredient and a crystallizing agent, (2) a bypass pathway connected to the vessel for crystallization which can make a solution in the vessel for crystallization circulated, and (3) a pump set in the bypass pathway which can pressure the solution. In such device, the bypass pathway can connect, for example, from the vessel for crystallization to the pump, and from the pump to the vessel for crystallization, with tube, pipe, etc. The tube includes, for example, but not limited to, silicone tube, flexible polyvinyl chloride tube, polyurethane tube, fluoro-rubber tube, and olefinic tube, and preferably silicone tube.

The circulation velocity in the bypass pathway is preferably about n×0.001 L/min to about n×2 L/min, more preferably about n×0.01 L/min to about n×1 L/min wherein "n" denotes the total volume of the crystallizing agent and the solution of the active ingredient. In more detail, the circulation velocity is about 1 mL/min to about 2000 mL/min, preferably about 10 mL/min to about 1000 mL/min when the total volume of the crystallizing agent and the solution of the active ingredient is 1 L; about 100 mL/min to about 200 L/min, preferably about 1 L/min to about 100 L/min when the total volume of the crystallizing agent and the solution of the active ingredient is 100 L; and about 1 L/min to about 2000 L/min, preferably about 10 L/min to about 1000 L/min when the total volume of the crystallizing agent and the solution of the active ingredient is 1000 L.

Step (4):

The crystal precipitated in step (3) is collected through a filter. The crystal produced under the condition of in step (3) such as crystallizing temperature, circulation velocity and stirring speed has almost uniform mean particle sizes. The method therefore can prepare a crystal having uniform mean particle sizes without any milling steps.

Step (5):

A water solution (vehicle solution) comprising a surfactant, a buffer, an isotonic agent, and water for injection is prepared. The vehicle solution may further comprise a pH regulator, a soothing agent, a water-soluble polymer, and other polymers, etc. With the resulting vehicle solution, the crystal of step (4) is washed. The washing process may be repeated several times. After washing the crystal, the vehicle solution can be put into the vessel again and mixed with the crystal to provide a suspension formulation which is the formulation of the invention. In addition, the active ingredient prepared in step (4) may be continuously suspended in the vehicle solution to provide an injectable product (suspension formulation), and additionally, the active ingredient obtained from the crystallization may be washed with water, an organic solvent or a mixture thereof, and then dried for a while and suspended in the vehicle solution again to prepare a suspension formulation.

The suspension formulation prepared in Step (5) can be formed as a prefilled formulation through the following step (6).

Step (6):

The suspension formulation prepared in Step (5) is put into a container for formulation such as a prefilled syringe, a vial, an ampule, a bag or a Blow-Fill-Seal container. The preferred container includes a prefilled syringe and a vial.

Step (7):

The prefilled formulation of the suspension (i.e. container filled with the suspension) prepared in step (6) is sterilized by a process of steaming under pressure. The process can make the level of sterile assurance enhanced.

The temperature of the steam sterilization under pressure (high-pressure steam sterilization) is preferably 100-150° C., more preferably 115-141° C., and even more preferably 115-126° C. The time for the steam sterilization under pressure can be suitably decided, for example, 1-120 min, more preferably 5-60 min, even more preferably 10-40 min.

Step (8):

The prefilled formulation of the suspension (i.e. container filled with the suspension) prepared in step (6) or (7) is ultrasonicated. The process can make the uniformity enhanced to enhance the re-suspensiblility when used.

The frequency of the ultrasonication is preferably 10-200 kHz, more preferably 20-100 kHz, and even more preferably 25-80 kHz. The time for the ultrasonication can be suitably decided, for example, 0.1-120 min, more preferably 0.1-60 min, even more preferably 0.1-30 min.

It is possible to do any one of the above steps (7) and (8) or both as needed. When step (7) is carried out, it is preferred to do step (8) to uniform the suspension since the active ingredient (free form of Compound 1) contains macroaggregated particles generated due to secondary aggregation (see, for example, Example A2, FIGS. 4 and 5 mentioned below).

Preparation Method B'

Steps (1)-(6) defined in Preparation Method A are carried out and further any one or both of Step (7) and (8) defined in Preparation Method B are carried out.

According to the above Preparation Method B' comprising Step (7), the level for aseptic assurance of the final product can be ensured since Steps (1)-(6) are aseptically carried out, and further the product prepared in Steps (1)-(6) is sterilized by a process of steaming under pressure in Step (7).

In addition, it is also possible to prepare a similar sustained release formulation for injection from a physically-milled or spray-dried material of the present compound by means of step (5). Furthermore, the aseptic level of the formulation can be enhanced by carrying out Steps (6), (7) and (8).

Tables 1 and 2 show some typical examples of the sustained release formulation for injection. The examples listed in Tables 1 and 2 including examples which have combinations of the amount of each ingredient are preferable, but the scope of the present invention is not limited thereto.

TABLE 1

| Ingredients | 200 mg/mL | 300 mg/mL | 400 mg/mL | 600 mg/mL |
|---|---|---|---|---|
| Active ingredient (free form of Compound 1) | 200 mg | 300 mg | 400 mg | 600 mg |
| Polysorbate 80 | 1.7 mg | 1.5 mg | 1.3 mg | 0.9 mg |
| Sodium dihydrogen-phosphate (dihydrate) | 1.2 mg | 1.0 mg | 0.9 mg | 0.6 mg |
| Disodium hydrogen-phosphate (anhydride) | 2.2 mg | 1.9 mg | 1.7 mg | 1.2 mg |
| Sodium chloride | 5.8 mg | 5.2 mg | 4.6 mg | 3.2 mg |
| Water for injection | 1 mL (total volume) | | | |
| pH | 7 | | | |
| Osmotic pressure ratio | 1 | | | |
| Mean particle size | 5-25 μm, more preferably 5-20 μm | | | |

TABLE 2

| Ingredients | 50 mg/mL | 100 mg/mL | 150 mg/mL |
|---|---|---|---|
| Active ingredient (free form of Compound 1) | 50 mg | 100 mg | 150 mg |
| Polysorbate 80 | 2.0 mg | 1.9 mg | 1.8 mg |
| Sodium dihydrogenphosphate(dihydrate) | 1.4 mg | 1.3 mg | 1.2 mg |
| Disodium hydrogenphosphate(anhydride) | 2.6 mg | 2.4 mg | 2.3 mg |
| Sodium chloride | 6.9 mg | 6.5 mg | 6.2 mg |
| Water for injection | 1 mL (total volume) | | |
| pH | 7 | | |
| Osmotic pressure ratio | 1 | | |
| Mean particle size | 5-25 μm | | |

EXAMPLES

The present invention is illustrated in more detail by the following examples, but it should not be construed to be limited thereto.

Example 1

Preparation of Formulation No. 1

Step (1):

To an aqueous 70% ethanol solution containing 1% (w/v) polysorbate 80, N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide hydrochloride (Compound 1) was dissolved so that the concentration of Compound 1 should be 2% (w/v), and then the solution was sterilely filtered through Millipak™ 60 (model: MPGL06 GH2, pore diameter=0.22 μm, MILLIPORE) to prepare 5200 mL of a solution of the active ingredient.

Step (2):

Meanwhile, a water solution of 0.7% (w/v) disodium hydrogenphosphate (anhydride)/1% (w/v) polysorbate 80 was sterilely filtered through Millipak™ 60 (pore diameter=0.22 μm, MILLIPORE) to prepare 5200 g of a crystallizing agent.

Step (3): Process of Crystallization

To a 1 L glass vessel [model: GLS-80 DURAN™, SCHOTT; with a teflon stirring bar (ϕ 15 mm×70 mm)], 500 g of the crystallizing agent was sterilely injected. Then, maintaining the sealed state of the vessel at a crystallizing temperature of around 25° C., the solution of the active ingredient was added dropwise to the glass vessel at a flow rate of 50 mL/min for 10 minutes while stirring the reaction with a magnetic stirrer (model: BS-190N, IWAKI) at a stirring speed of 750 rpm to give a crystal slurry of the active ingredient. The crystal in the slurry was a cubic-shaped crystal which was a free form of Compound 1.

Step (4):

The crystal slurry was injected to a pressurized filter system (SUS316; model: SF-145, ADVANTEC) under the sealed state to be filtered through a supported PTFE membrane filter pre-attached to the filter system (model: 13110014, pore diameter=1 μm, ADVANTEC), then the crystal of the active ingredient was collected on the filter, and the liquid ingredients were removed.

Step (5):

To the crystal of the active ingredient which was collected on the filter, a vehicle solution (about pH 7) comprising sterilely-filtered 0.14% (w/v) sodium dihydrogenphosphate (dihydrate)/0.26% (w/v) disodium hydrogenphosphate (anhydride)/0.70% (w/v) sodium chloride/0.20% (w/v) polysorbate 80 was sterilely injected, and then the mixture was re-suspended, and filtered. After repeating this procedure several times, the vehicle solution was injected thereto again to prepare the desired formulation. The injection volume of the vehicle solution was decided according to "400 mg/mL" in Table 1 so that each ingredient could be adapted to the amount calculated based on its density to prepare 400 mg/mL sustained-release formulation for injection defined in Table 1.

Example 2

Preparation of Formulation No. 2

According to substantially the same procedure as described in Example 1 [Steps (3) to (5)] except that the stirring speed of the magnetic stirrer was 675 rpm, using 500 g of the crystallizing agent and 500 mL of the solution of the active ingredient which were prepared in Example 1, 400 mg/mL sustained-release sterile formulation defined in Table 1 was prepared. The injection volume of the vehicle solution was decided according to "400 mg/mL" in Table 1 so that each ingredient could be adapted to the amount calculated based on its density to prepare 400 mg/mL sustained-release formulation for injection defined in Table 1.

Example 3

Preparation of Formulation No. 3

According to substantially the same procedure as described in Example 1 [Steps (3) to (5)] except that the stirring speed of the magnetic stirrer was 400 rpm, using 500 g of the crystallizing agent and 500 mL of the solution of the active ingredient which were prepared in Example 1, 400 mg/mL sustained-release sterile formulation defined in Table 1 was prepared. The injection volume of the vehicle solution was decided according to "400 mg/mL" in Table 1 so that each ingredient could be adapted to the amount calculated based on its density to prepare 400 mg/mL sustained-release formulation for injection defined in Table 1.

Example 4

Measurement of Particle Size Distribution of Formulations No. 1 to No. 3

Table 3 shows the formulation compositions of Formulations No. 1 to No. 3 which were respectively prepared in Examples 1 to 3.

TABLE 3

| Formulation composition | |
|---|---|
| Active ingredient (free form of Compound 1) | 400 mg |
| Polysorbate 80 | 1.3 mg |
| Sodium dihydrogenphosphate dihydrate | 0.9 mg |
| Disodium hydrogenphosphate anhydride | 1.7 mg |
| Sodium chloride | 4.6 mg |
| Water for injection | 1 mL (total volume) |

(Measurement of Particle Size Distribution)

The particle size distribution was determined as a volume basis with a laser diffraction particle size analyzer (model: SALD-3000, Shimadzu Corporation) by wet method using water as a dispersion medium (refractive index: 2.40-0.20 i). The resulting particle size was expressed as a mean particle size (D50) based on its median diameter.

Table 4 shows the particle size distributions (D10, D50, D90) of Formulations No. 1 to No. 3. These results indicate that it is possible to control the mean particle size of the crystalline active ingredient by changing the stirring speed of the magnetic stirrer, unless the crystallizing temperature, and the fluid volumes of the crystallizing agent and the solution of the active ingredient are varied.

TABLE 4

| Formulation No. | Stirring speed (rpm) | Particle size distribution (μm) | | |
|---|---|---|---|---|
| | | D10 | Mean particle size D50 | D90 |
| 1 | 750 | 5.4 | 11.1 | 19.5 |
| 2 | 675 | 8.1 | 15.2 | 21.1 |
| 3 | 400 | 15.0 | 19.9 | 25.1 |

Example 5

To an aqueous 70% ethanol solution containing 1% (w/v) polysorbate 80, Compound 1 was dissolved so that the concentration of Compound 1 should be 2% (w/v), and then the solution was sterilely filtered through Millipak™ 60 (pore diameter=0.22 μm) to prepare 5200 mL of a solution of the active ingredient.

Meanwhile, a water solution of 0.7% (w/v) disodium hydrogenphosphate (anhydride)/1% (w/v) polysorbate 80 was sterilely filtered through Millipak™ 60 (pore diameter=0.22 μm) to prepare 5000 g of a crystallizing agent.

To a 10 L glass vessel [ϕ 220 mm×430 mm, caliber ϕ 95 mm, IWAKI; with a teflon stirring bar for magnetic stirrer (ϕ 27 mm×108 mm)] whose inside is sterilized, 5000 g of the crystallizing agent was injected. Then, at a crystallizing temperature of around 25° C., the solution of the active ingredient was added dropwise to the glass vessel at a flow rate of 500 mL/min for 10 minutes while stirring the reaction with a magnetic stirrer (model: BS -190N, IWAKI) at a stirring speed of 650 rpm to give a crystal slurry of the active ingredient. The crystal in the slurry was a cubic-shaped crystal which was a free form of Compound 1.

According to substantially the same procedure as described in Example 1 [Step (5)], adjusting the concentration of the active ingredient by changing the injection volume of the vehicle solution, 300 mg/mL sustained-release formulation for injection defined in Table 1 was prepared.

The particle size distributions were 5.6 μm (D10), 7.6 μm (mean particle size D50), and 11.7 μm (D90), which were determined by using the method measuring particle size distributions defined in Example 4.

Example 6

Preparation of Formulation No. 4 and Formulation No. 7

To an aqueous 70% ethanol solution containing 1% (w/v) polysorbate 80, Compound 1 was dissolved so that the concentration of Compound 1 should be 2% (w/v), and then the solution was sterilely filtered through Millipak™ 100 (model: MPGL1GCA3, pore diameter=0.22 μm, MILLIPORE) to prepare 5200 mL of a solution of the active ingredient.

Meanwhile, a water solution of 0.7% (w/v) disodium hydrogenphosphate (anhydride)/1% (w/v) polysorbate 80 was sterilely filtered through Millipak™ 100 (pore diameter=0.22 μm) to prepare 5200 g of a crystallizing agent.

To a 1 L glass bottle [model: GLS-80 DURAN™, SCHOTT; with a teflon stirring bar (ϕ 15 mm×70 mm)] whose inside is sterilized, 600 g of the crystallizing agent was sterilely injected. Then, at a crystallizing temperature of around 1° C. (in ice bath), the solution of the active ingredient was added dropwise to the glass bottle at a flow rate of 60 mL/min for 10 minutes while stirring the reaction with a magnetic stirrer (model: BS-190N, IWAKI) at a stirring speed of 500 rpm to give a crystal slurry of the active ingredient. The crystal in the slurry was a cubic-shaped crystal which was a free form of Compound 1.

According to substantially the same procedure as described in Example 1 [Step (5)], adjusting the concentration of the active ingredient by changing the injection volume of the vehicle solution, 200 mg/mL (Formulation No. 4) and 400 mg/mL (Formulation No. 7) sustained-release formulations for injection defined in Table 1 were prepared.

Example 7

Preparation of Formulations No. 5 and No. 8

Into a 10 L glass bottle (ϕ 220 mm×430 mm, caliber ϕ 95 mm, IWAKI) whose inside is sterilized, stirring wings (diameter=70 mm, 4 inclined wings, material=SUS304) were sterilely set. Then, under a sterile condition, the crystallizing agent (2500 g) and the solution of the active ingredient (2500 mL) which were prepared in Example 6 were continuously added at a flow rate of 300 mL/min while mixing them with a Y shaped tube (full length=60 mm, internal diameter=6 mm) to the glass bottle wherein the crystallizing temperature was controlled at 25° C. At the time that about 1 L of the mixture was added thereto (i.e. when the stirring wings started to soak the mixture), the stirring at 200 rpm was started with a stirring machine (model: STIRRER SSR, IWAKI). After all of the crystallizing agent and the solution of the active ingredient were added while mixing continuously, the reaction was stirred for another about 15 minutes to give a crystal slurry of the active ingredient. The crystal in the crystal slurry was a cubic-shaped crystal which was a free form of Compound 1.

Similarly, according to the same procedure as described in Example 1 [Step (5)], 200 mg/mL (Formulation No. 5) and 400 mg/mL (Formulation No. 8) sustained-release formulations for injection in Table 1 were prepared by adjusting the volume of the vehicle solution so that the concentration of the active ingredient could be adapted for the desired value.

Example 8

Preparation of Formulation No. 6

To a 2 L glass bottle [model: GLS-80 DURAN™, SCHOTT; with a teflon stirring bar (φ 15 mm×70 mm)] whose inside is sterilized, 1100 g of the crystallizing agent prepared in Example 6 was sterilely injected. Then, the solution of the active ingredient prepared in Example 7 was sterilely added dropwise at a flow rate of 110 mL/min for 10 minutes to the glass bottle wherein the crystallizing temperature was controlled at 40° C. while stirring with a magnetic stirrer (model: BS-190N, IWAKI) at a stirring speed of 600 rpm to give a crystal slurry of the active ingredient. The crystal in the crystal slurry was a cubic-shaped crystal which was a free form of Compound 1.

According to substantially the same procedure as described in Example 1 [Step (5)], adjusting the concentration of the active ingredient by changing the injection volume of the vehicle solution, the 200 mg/mL sustained-release formulation for injection defined in Table 1 was prepared.

Example 9

Preparation of Formulation No. 9

To a 1 L glass bottle [model: GLS-80 DURAN™, SCHOTT; with a teflon stirring bar (φ 15 mm×70 mm)] whose inside is sterilized, 400 g of the crystallizing agent prepared in Example 6 was sterilely injected. Then, the solution of the active ingredient prepared in Example 6 was sterilely added dropwise at a flow rate of 40 mL/min for 10 minutes to the glass bottle wherein the crystallizing temperature was controlled at 50° C. while stirring with a magnetic stirrer (model: BS-190N, IWAKI) at a stirring speed of 400 rpm to give a crystal slurry of the active ingredient. The crystal in the crystal slurry was a cubic-shaped crystal which was a free form of Compound 1.

According to substantially the same procedure as described in Example 1 [Step (5)], adjusting the concentration of the active ingredient by changing the injection volume of the vehicle solution, the 400 mg/mL sustained-release formulation for injection defined in Table 1 was prepared.

Example 10

Preparation of Formulation No. 10

The free form of Compound 1 was milled with a Pin Mill (model AVIS-100, DALTON) at a blade rotational speed of 14000 rpm to give a milled active ingredient. To the milled active ingredient, the sterilely-filtered vehicle solution was sterilely injected and the mixture was re-suspended, and then the concentration of the active ingredient was adjusted by changing the injection volume of the vehicle solution to give the 400 mg/mL sustained-release formulation for injection defined in Table 1.

Example 11

Preparation of Formulation No. 11

To a 70% ethanol solution containing 1% (w/v) polysorbate 80, Compound 1 was dissolved so that the concentration of Compound 1 should be 2% (w/v), and then the solution was sterilely filtered through SFCA Bottle Top Filter™ [a bottle-top filter system with cellulose acetate membrane, model: 291-4520, pore diameter=0.22 µm, Nalge Nunc International] to prepare 5000 mL of a solution of the active ingredient.

Meanwhile, a water solution of 0.7% (w/v) disodium hydrogenphosphate (anhydride)/1% (w/v) polysorbate 80 was sterilely filtered through SFCA Bottle Top Filter™ [pore diameter=0.22 µm] to prepare 5000 g of a crystallizing agent.

To a 300 mL tall beaker [model: TE-32, IWAKI; with a teflon stirring bar (φ 10 mm×35 mm)], 100 mL of the crystallizing agent was injected. Then, the solution of the active ingredient was added dropwise to the beaker at a flow rate of 10 mL/min for 10 minutes while controlling the crystallizing temperature at 80° C. and stirring with a magnetic stirrer (model: BS-56L-1, IWAKI) at a stirring speed of 1200 rpm to give a crystal slurry of the active ingredient. The crystal in the crystal slurry was a cubic-shaped crystal which was a free form of Compound 1.

According to substantially the same procedure as described in Example 1 [Steps (4) to (5)], adjusting the concentration of the active ingredient by changing the injection volume of the vehicle solution, the 400 mg/mL sustained-release sterile formulation defined in Table 1 was prepared, which is also the same as the formulation defined in Table 3.

The particle size distribution was 20.8 µm (D10), 54.3 µm (mean particle size D50), and 130.3 µm (D90), which were determined by using the method measuring particle size distributions defined in Example 4.

The sterile formulation of the present invention can be prepared through the non-sterile process of any one of Examples 1 to 11, and then steam sterilization under pressure and ultrasonication (according to, for example, the method of Example A1, B3 or B4).

Example A1

To an aqueous 70% ethanol solution containing 1% (w/v) polysorbate 80, Compound 1 was dissolved so that the concentration of Compound 1 should be 2% (w/v), and then the solution was sterilely filtered through Millipak™ 60 (pore diameter=0.22 µm) to prepare 10500 mL of a solution of the active ingredient. Meanwhile, a water solution of 0.7% (w/v) disodium hydrogenphosphate (anhydride)/1% (w/v) polysorbate 80 was filtered through Millipak™ 60 (pore diameter=0.22 µm) to prepare 10500 g of a crystallizing agent.

To a 10 L glass vessel [φ 220 mm×430 mm, caliber φ 95 mm, IWAKI; with a teflon stirring bar (φ 27 mm×108 mm)] whose inside is sterilized, 5000 g of the above crystallizing agent was injected. Then, at a crystallizing temperature of around 25° C., the solution of the active ingredient was added dropwise to the glass vessel at a flow rate of 500 mL/min for 10 minutes while stirring the reaction with a magnetic stirrer (model: BS-190N, IWAKI) at a stirring speed of 650 rpm to give a crystal slurry of the active ingredient. Using the above 10 L glass vessel, the above procedure was repeated twice to obtain the crystal slurry of the active ingredient whose total amount was 20 L. The crystal in the slurry was a cubic-shaped crystal which was a free form of Compound 1.

The crystal slurry was injected to a pressurized filter system (model: SF-145, material=SUS316, ADVANTEC) to be filtered through a supported PTFE membrane filter pre-attached to the filter system (model: 13110014, pore diameter=1 μm, ADVANTEC), then the crystal of the active ingredient was collected on the filter, and the liquid ingredients were removed.

To the crystal of the active ingredient which was collected on the filter, a vehicle solution (about pH 7) comprising sterilely-filtered 0.14% (w/v) sodium dihydrogenphosphate (dihydrate)/0.26% (w/v) disodium hydrogenphosphate (anhydride)/0.70% (w/v) sodium chloride/0.20% (w/v) polysorbate 80 was injected, and then the mixture was re-suspended, and filtered. After repeating this procedure several times, the vehicle solution was injected thereto again to prepare the desired formulation. The injection volume of the vehicle solution was decided according to Table 1 so that each ingredient could be adapted to the amount calculated based on its density to prepare 100, 150 and 200 mg/mL sustained-release formulation for injection defined in Table 1.

Each 2 mL of the sustained release formulations for injection wherein the concentrations of the active ingredient are 100, 150, and 200 mg/mL were put into each 4 mL vial (model: V-SC4 mL CS, FUJI GLASS), and the vials were sealed with a rubber stopper and a cap. One mL prefilled syringe (model: V-OVS System 10.6 rubber formulation 40, VETTER) was filled with 1 mL of the sustained release formulation for injection wherein the concentration of the active ingredient is 150 mg/mL and sealed with a rubber stopper (ST-W 1 mL, VETTER). The vials and the prefilled syringe were sterilized at 121° C. for 20 min with a high-pressure steam sterilizer (model: HG-80, HIRAYAMA). Then, the vials and the prefilled syringe were treated for 3 min with an ultrasonicator (model: UT-605HS, SHARP) at 35 kHz.

The particle size distribution was 5.6 μm (D10), 10.3 μm (mean particle size D50) and 16.9 μm (D90) in 100 mg/mL formulation laded in vial; 5.6 μm (D10), 8.6 μm (mean particle size D50) and 13.1 μm (D90) in 150 mg/mL formulation laded in vial; 5.7 μm (D10), 8.7 μm (mean particle size D50) and 13.9 μm (D90) in 200 mg/mL formulation laded in vial; and 9.9 μm (D10), 22.1 μm (mean particle size D50) and 43.2 μm (D90) in 150 mg/mL formulation laded in prefilled syringe, which were determined by using the method measuring particle size distributions defined in Example 4.

Example A2

Using the sustained release formulation for injection (in vial) comprising 150 mg/mL crystalline active ingredient which was just sterilized with a high-pressure steam sterilizer in Example A1, (i) non-ultrasonicated formulation (FIG. 4), and (ii) ultrasonicated formulation (35 kHz, 3 min) (FIG. 5) were stirred for 30 sec with a vortex mixer (model: MT-51, Yamato), and transferred each to 35 mm polystyrene plate (model: 1000-035, IWAKI). The formulations were observed with the naked eye if they contain macroaggregated particles.

Figure 4:
FIG. 4 is a photograph showing that the non-ultrasonicated formulation prepared in Example A2 contains macroaggregated particles.
Figure 5:
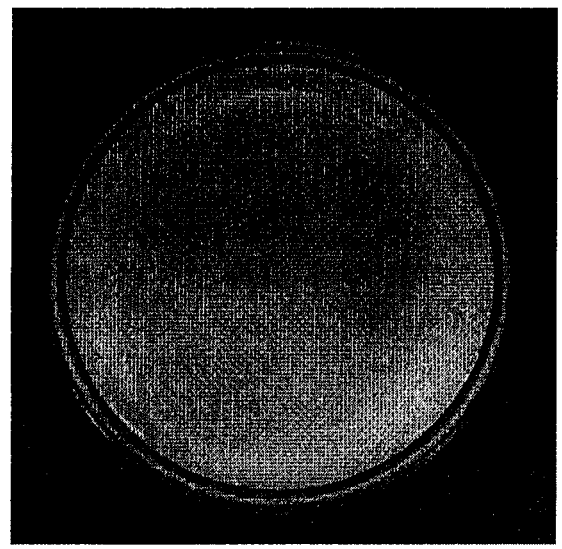
FIG. 5 is a photograph showing that the ultrasonicated formulation (35 kHz, 3 min) prepared in Example A2 contains no macroaggregated particles.

The results showed that there were many secondarily-aggregated macroaggregated particles in (i) non-ultrasonicated formulation as shown in FIG. 4, while there were no secondarily-aggregated macroaggregated particles in (ii) ultrasonicated formulation (35 kHz, 3 min). Thus, like the ultrasonicated formulation, it became possible to prepare a sustained release formulation for injection which has uniform crystal of an active ingredient.

Example A3

Powder X-Ray Diffraction

Using the sustained release formulation for injection (in vial) comprising 150 mg/mL crystalline active ingredient which was prepared in Example A1, the powder X-ray diffraction was measured (i) before the steam sterilization under pressure, and (ii) after the steam sterilization under pressure (121° C., 20 min) and the ultrasonication (35 kHz, 3 min).

The measurement of powder X-ray diffraction was carried out with an X-ray diffraction measurement device [model: X'pert Pro, CuKα source (λ=1.54056 Å), Kevex solid phase Si(Li) ditector, Spectris]. The condition of the measurement was Start angle: 5.0°, End angle: 40.0°, Step size: 0.017°, Time per step: 5.1 sec, Scan speed: 0.42°/sec, X-ray: 45 kV, 40 mA, slit (FDS, FASS): ½, 1, mask: 15. The crystal of the active ingredient was washed with water for injection (Otsuka Parmaceutical) and dried in air overnight. The resulting dried crystal powder was put on the top of a sample holder and the surface thereof was smoothed with a glass slide.

Figure 6:
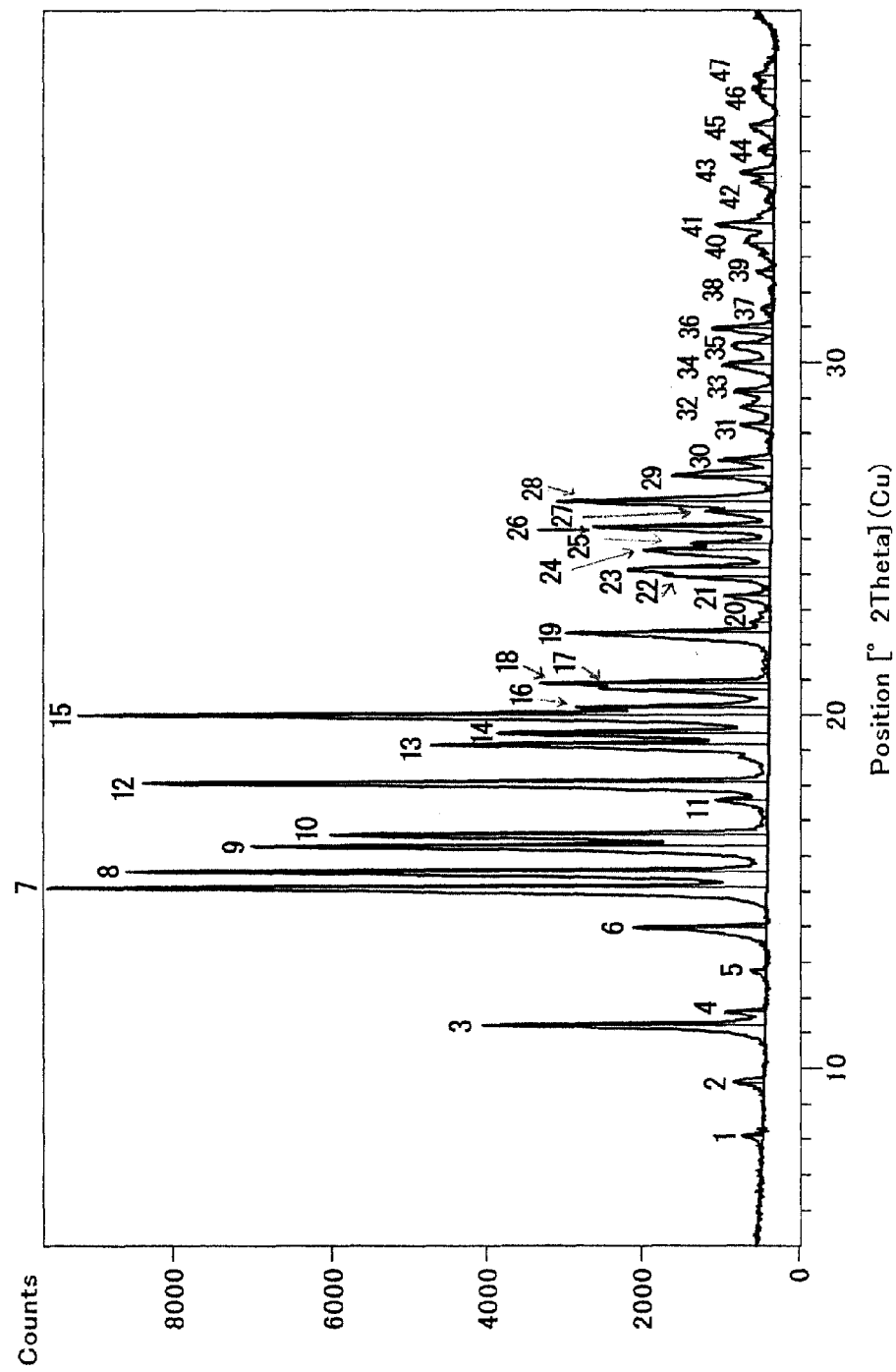
FIG. 6 is an X-ray diffraction in the sample before the steam sterilization under pressure in Example A3.
Figure 7:
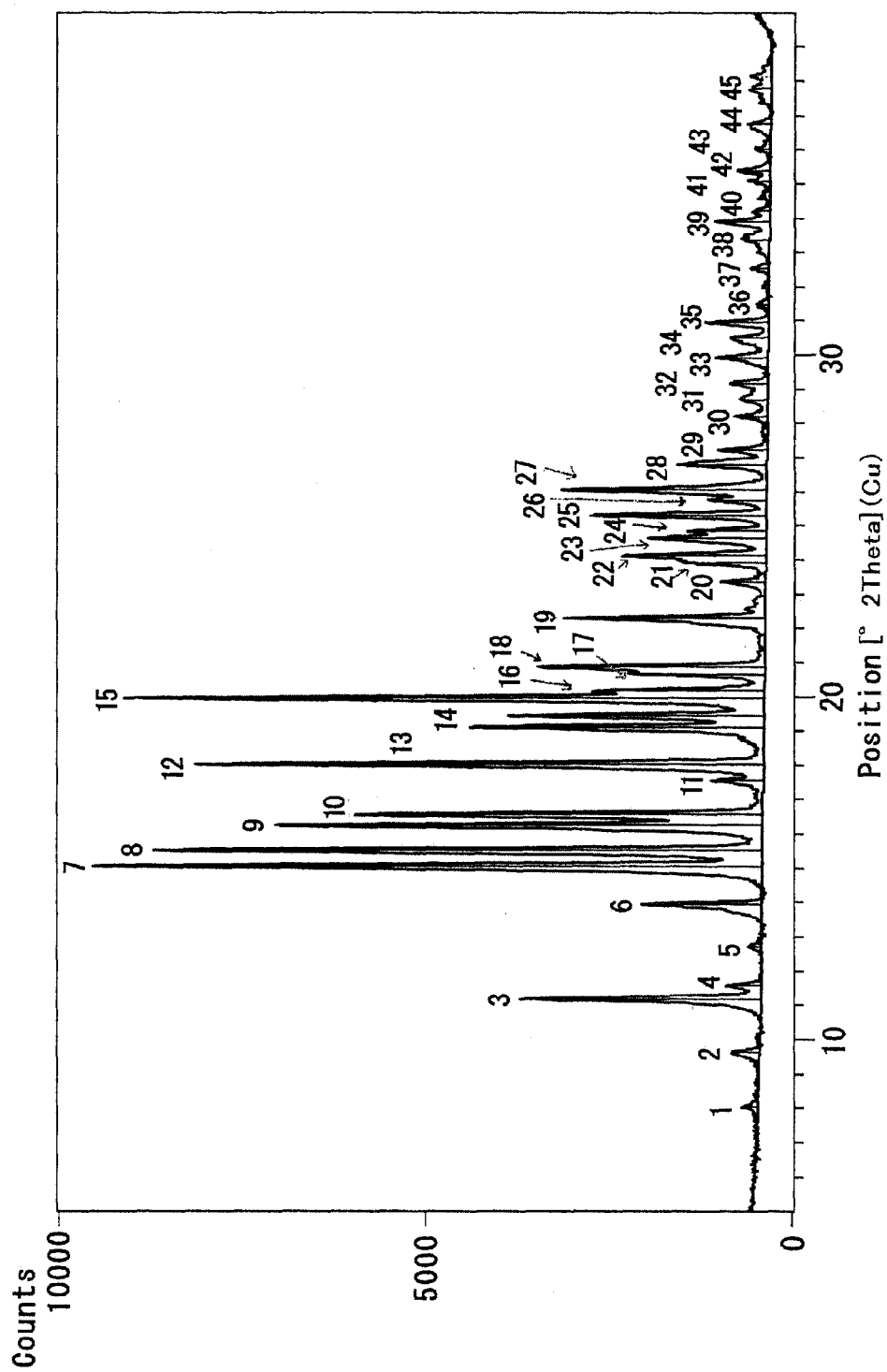
FIG. 7 is an X-ray diffraction in the sample after the steam sterilization under pressure (121° C., 20 min) and the ultrasonication (35 kHz, 3 min) in Example A3.

In the sustained release formulation for injection comprising 150 mg/mL crystalline active ingredient, the result of X-ray diffraction in the sample before the steam sterilization under pressure is shown in Table 5 and FIG. 6, and the result of X-ray diffraction in the sample after the steam sterilization under pressure (121° C., 20 min) and the ultrasonication (35 kHz, 3 min) is shown in Table 6 and FIG. 7.

There was no substantial change in the powder X-ray diffraction between the samples before the steam sterilization under pressure and after the steam sterilization under pressure and the ultrasonication.

TABLE 5

(before the steam sterilization under pressure)

| No. | 2θ [°] | d-spacing [Å] | Relative Intensity [%] |
| --- | --- | --- | --- |
| 3 | 11.2 | 7.87 | 38.9 |
| 6 | 14.0 | 6.33 | 18.4 |
| 7 | 15.1 | 5.86 | 100.0 |
| 8 | 15.6 | 5.69 | 90.3 |
| 9 | 16.3 | 5.44 | 73.7 |
| 10 | 16.6 | 5.34 | 61.1 |
| 12 | 18.1 | 4.91 | 86.9 |
| 13 | 19.2 | 4.63 | 47.5 |
| 14 | 19.5 | 4.55 | 37.7 |
| 15 | 20.0 | 4.44 | 98.2 |
| 16 | 20.2 | 4.40 | 27.3 |
| 17 | 20.7 | 4.29 | 23.8 |
| 18 | 20.9 | 4.25 | 33.0 |
| 19 | 22.3 | 3.98 | 28.7 |
| 22 | 23.9 | 3.72 | 12.1 |
| 23 | 24.2 | 3.68 | 19.7 |

TABLE 5-continued (before the steam sterilization under pressure)

| No. | 2θ [°] | d-spacing [A] | Relative Intensity [%] |
|---|---|---|---|
| 24 | 24.7 | 3.61 | 17.2 |
| 25 | 24.9 | 3.58 | 11.3 |
| 26 | 25.4 | 3.51 | 25.3 |
| 28 | 26.1 | 3.42 | 30.3 |
| 29 | 26.8 | 3.33 | 13.7 |

TABLE 6

[After the steam sterilization under pressure (121° C., 20 min) and the ultrasonication (35 kHz, 3 min)]

| No. | 2θ [°] | d-spacing [A] | Relative Intensity [%] |
|---|---|---|---|
| 3 | 11.2 | 7.91 | 36.46 |
| 6 | 13.9 | 6.35 | 18.06 |
| 7 | 15.1 | 5.88 | 100.00 |
| 8 | 15.5 | 5.70 | 90.50 |
| 9 | 16.3 | 5.46 | 73.50 |
| 10 | 16.6 | 5.35 | 61.58 |
| 12 | 18.0 | 4.92 | 84.94 |
| 13 | 19.1 | 4.64 | 44.32 |
| 14 | 19.5 | 4.56 | 38.45 |
| 15 | 20.0 | 4.45 | 96.31 |
| 16 | 20.2 | 4.40 | 24.46 |
| 17 | 20.7 | 4.30 | 19.77 |
| 18 | 20.9 | 4.26 | 34.27 |
| 19 | 22.3 | 3.99 | 29.46 |
| 21 | 23.9 | 3.72 | 10.77 |
| 22 | 24.1 | 3.69 | 21.13 |
| 23 | 24.6 | 3.61 | 17.81 |
| 24 | 24.9 | 3.58 | 11.59 |
| 25 | 25.3 | 3.52 | 26.46 |
| 27 | 26.0 | 3.42 | 30.81 |
| 28 | 26.8 | 3.33 | 11.85 |

Based on the results of powder X-ray diffraction after the steam sterilization under pressure and the ultrasonication (Table 6 and FIG. 7), the specified main and characteristic diffraction peaks are listed below. The values of diffraction peaks at diffraction angle 2θ (°) can include a little measurement errors according to a measurement device or a measurement condition. For example, the measurement error may be ±0.2, preferably ±0.1.

Main diffraction peaks: 2θ (°)=11.2, 15.1, 15.5, 16.3, 16.6, 18.0, 19.1, 19.5, 20.0, 20.9, 22.3, 26.0.

Characteristic diffraction peaks: 2θ (°)=15.1, 15.5, 16.3, 16.6, 18.0, 20.0.

Example B1

Without Bypass Pathway

To an aqueous 70% ethanol solution containing 1% (w/v) polysorbate 80, Compound 1 was dissolved so that the concentration of Compound 1 should be 2% (w/v), and then the solution was sterilely filtered through Millipak™ 60 (pore diameter=0.22 μm) to prepare 10 L of a solution of the active ingredient.

Meanwhile, a water solution of 0.7% (w/v) disodium hydrogenphosphate (anhydride)/1% (w/v) polysorbate 80 was sterilely filtered through Millipak™ 60 (pore diameter=0.22 μm) to prepare 10 kg of a crystallizing agent.

Into a 1 L glass separable flask (ϕ 110 mm×180 mm), stirring wings (diameter=70 mm, 4 wings whose inclination is 45°, material=SUS304) were set. The crystallizing agent (500 mL) was injected into the 1 L glass separable flask. Then, the solution of the active ingredient was added dropwise at a flow rate of 20 mL/min to the flask wherein the crystallizing temperature was controlled at around 25° C. while mixing them at 400 rpm with a stirring machine (model: FBL1200, Shinto Scientific) for 25 min to give a crystal slurry of the active ingredient. The crystal in the crystal slurry was a mixture of a cubic-shaped crystal and an amorphous form which was a free form of Compound 1.

Example B2

With Bypass Pathway

Into a 1 L glass separable flask (ϕ 110 mm×180 mm), stirring wings (diameter=70 mm, 4 inclined wings, material=SUS304) were set, and a bypass pathway composed of silicon tube (model: 96410-15, Cole-Parmer), roller pump (model: 7549-32, Cole-Parmer) and pump head (model: 77201-62, Cole-Parmer) was set.

The crystallizing agent (500 mL) prepared in Example B1 was injected into the 1 L glass separable flask. Then, the solution of the active ingredient prepared in Example B1 was added dropwise at a flow rate of 20 mL/min to the flask wherein the crystallizing temperature was controlled at around 25° C. while mixing them at 400 rpm with a stirring machine (model: FBL1200, Shinto Scientific) for 25 min and simultaneously circulating the solution for 25 min or more at a circulation velocity of 600 mL/min (roller pump, flow rate: 150 mL/min×4 pump heads, model: 7523-00, Cole-Parmer) via the above bypass pathway to give a crystal slurry of the active ingredient. The crystal in the crystal slurry was a cubic-shaped crystal which was a free form of Compound 1.

Example B3

With Bypass Pathway

To an aqueous 70% ethanol solution containing 1% (w/v) polysorbate 80, Compound 1 was dissolved so that the concentration of Compound 1 should be 2% (w/v), and then the solution was sterilely filtered through Millipak™ 100 (pore diameter=0.22 μm) to prepare 15.5 L of a solution of the active ingredient.

Meanwhile, a water solution of 0.7% (w/v) disodium hydrogenphosphate (anhydride)/1% (w/v) polysorbate 80 was filtered through Millipak™ 100 (pore diameter=0.22 μm) to prepare 15.5 kg of a crystallizing agent.

Into a 35 L SUS316L vessel (ϕ 330 mm×550 mm), stirring wings (diameter=120 mm, 3 wings whose inclination is 45°, material=SUS316L, SANKO ASTEC) were set, and a sealed-type bypass pathway composed of silicon tube (model: 96410-15, Cole-Parmer), roller pump (model: 7549-32, Cole-Parmer) and pump head (model: 77201-62, Cole-Parmer) was set. The crystallizing agent (15 kg) was injected into the vessel. Then, maintaining the sealed state of the vessel, the solution of the active ingredient was added dropwise at a flow rate of 600 mL/min to the vessel wherein the crystallizing temperature was controlled at around 25° C. while mixing them at 800 rpm (setting pressure: 0.2 MPa) with a stirring machine with air-motor (model: MRV003A, MAGNEO GIKEN) for 25 min and simultaneously circulating the solution for 25 min or more at a circulation velocity of 5.4 L/min (roller pump, flow rate: 900 mL/min×6 pump heads) via the above bypass pathway to give a crystal slurry of the active ingredient. The crystal in the crystal slurry was a cubic-shaped crystal which was a free form of Compound 1.

The substantially same process as Example 1 (Steps 4-5) was done by adjusting the volume of the vehicle solution to adjust the concentration of the active ingredient, to prepare a sustained release formulation for injection which contains each ingredient used in the vehicle solution shown in Table 7 that was calculated based on the density of the formulation and 150 mg/mL crystal of the active ingredient.

Two mL of the sustained release formulations for injection wherein the concentration of the active ingredient is 150 mg/mL was put into 4 mL vial (model: V-SC4 mL CS, FUJI GLASS), and the vial was sealed with a rubber stopper and a cap. The vial was sterilized at 121° C. for 20 min with a high-pressure steam sterilizer (type: HG -80, HIRAYAMA). Then, the vial was treated for 3 min with an ultrasonicator (model: UT-605HS, SHARP) at 35 kHz.

The particle size distribution was 12.4 μm (D10), 16.7 μm (mean particle size D50) and 21.9 μm (D90), which were determined by using the method measuring particle size distributions defined in Example 4.

TABLE 7

Composition of formulation

| | |
|---|---|
| Active ingredient (free form of Compound 1) | 150 mg |
| Polysorbate 80 | 1.8 mg |
| Sodium dihydrogenphosphate dihydrate | 1.2 mg |
| Disodium hydrogenphosphate anhydride | 2.3 mg |
| Sodium chloride | 6.2 mg |
| Water for injection | Total 1 mL |

Example B4

With Bypass Pathway

To an aqueous 70% ethanol solution containing 1% (w/v) polysorbate 80, Compound 1 was dissolved so that the concentration of Compound 1 should be 2% (w/v), and then the solution was sterilely filtered through Millipak™ 100 (pore diameter=0.22 μm) to prepare 50 L of a solution of the active ingredient.

Meanwhile, a water solution of 0.7% (w/v) disodium hydrogenphosphate (anhydride)/1% (w/v) polysorbate 80 was filtered through Millipak™ 100 (pore diameter=0.22 μm) to prepare 50 kg of a crystallizing agent.

Into a 150 L SUS304 vessel (φ 544 mm×630 mm), stirring wings (diameter=120 mm, 3 wings whose inclination is 45°, material=SUS316L, SANKO ASTEC) were set, and a bypass pathway composed of silicon tube (model: 96420-82, Cole-Parmer), roller pump (model: 7549-32, Cole-Parmer) and pump head (model: 77601-10, Cole-Parmer) was set. The crystallizing agent (50 kg) was injected into the vessel. Then, the solution of the active ingredient was added dropwise at a flow rate of 2 L/min to the vessel wherein the crystallizing temperature was controlled at around 25° C. while mixing them at 800 rpm (setting pressure: 0.2 MPa) with a stirring machine with air-motor (model: MRV003A, MAGNEO GIKEN) for 25 min and simultaneously circulating the solution for 25 min or more at a circulation velocity of 9 L/min (roller pump, flow rate: 4.5 L/min×2 pump heads) via the above bypass pathway to give a crystal slurry of the active ingredient. The crystal in the crystal slurry was a cubic-shaped crystal which was a free form of Compound 1.

The substantially same process as Example 1 (Steps 4-5) was done by adjusting the volume of the vehicle solution to prepare a sustained release formulation for injection which contains each ingredient used in the vehicle solution shown in Table 7 that was calculated based on the density of the formulation and 150 mg/mL crystal of the active ingredient.

Two mL of the sustained release formulations for injection wherein the concentration of the active ingredient is 150 mg/mL was put into 4 mL vial (model: V-SC4 mL CS, FUJI GLASS), and the vial was sealed with a rubber stopper and a cap. The vial was sterilized at 121° C. for 20 min with a high-pressure steam sterilizer (type: HG -80, HIRAYAMA). Then, the vial was treated for 3 min with an ultrasonicator (model: UT-605HS, SHARP) at 35 kHz.

The particle size distribution was 14.3 μm (D10), 17.9 μm (mean particle size D50) and 23.0 μm (D90), which were determined by using the method measuring particle size distributions defined in Example 4.

As mentioned above, the crystallizing process was carried out while circulating the solution via the bypass pathway connected to the vessel for crystallization, and it was possible to reproducibly prepare a cubic crystal thereof with a pump in the bypass pathway such as a roller pump (tube pump, hose pump), a reciprocating pump (piston pump, plunger pump, diaphragm pump), and a rotary pump (gear pump, vane pump, screw pump) even when a large-scale preparation.

Example C1

Effect of Ethanol in Solution of the Active Ingredient (70% Ethanol-Containing Solution of the Active Ingredient)

To an aqueous 70% ethanol solution containing 1% (w/v) polysorbate 80 as a water-containing alcohol solvent, Compound 1 was dissolved so that the concentration of Compound 1 should be 2% (w/v), and then the mixture was well stirred to be dissolved as far as possible. Then, the solution was sterilely filtered through SFCA Bottle Top Filter™ (pore diameter=0.22 μm) to prepare 1000 mL of a 70% ethanol solution of the active ingredient.

Meanwhile, a water solution of 0.7% (w/v) disodium hydrogenphosphate (anhydride)/1% (w/v) polysorbate 80 was sterilely filtered through SFCA Bottle Top Filter™ (pore diameter=0.22 μm) to prepare 10 kg of a crystallizing agent.

Into a 1 L glass separable flask (φ 110 mm×180 mm), stirring wings (diameter=70 mm, 4 inclined wings, material=SUS304) were set, and a bypass pathway composed of silicon tube (model: 96410-15, Cole-Parmer), roller pump (model: 7549-32, Cole-Parmer) and pump head (model: 77201-62, Cole-Parmer) was set. The crystallizing agent (500 mL) was injected into the 1 L glass separable flask. Then, the solution of the active ingredient was added dropwise at a flow rate of 20 mL/min to the flask wherein the crystallizing temperature was controlled at around 25° C. while mixing them at 400 rpm with a stirring machine (model: FBL1200, Shinto Scientific) for 25 min and simultaneously circulating the solution for 25 min or more at a circulation velocity of 600 mL/min (roller pump, flow rate: 150 mL/min×4 pump heads, model: 7523-00, Cole-Parmer) via the above bypass pathway to give a crystal slurry of the active ingredient. The crystal in the crystal slurry was a cubic-shaped crystal which was a free form of Compound 1.

The crystal slurry was injected to a pressurized filter system (SUS316; model SF-145, ADVANTEC) to be filtered through a supported PTFE membrane filter pre-attached to the filter system (model: 13110014, pore diameter=1 µm, ADVANTEC), then the crystal of the active ingredient was collected on the filter, and the liquid ingredients were removed.

Water for injection (Otsuka Pharmaceutical) was injected on the crystal of the active ingredient collected on the filter, the crystal was re-suspended, and then the resulting crystal was collected. The procedure was repeated several times to wash the crystal of the active ingredient. The crystal of the active ingredient collected on the supported PTFE membrane filter was dried at 60° C. for 4 hours, the weight of the crystal was weighed (10.51 g, yield: 97.3% from 10.8 g of the starting material).

The particle size distribution was 5.5 µm (D10), 10.5 µm (mean particle size D50) and 18.9 µm (D90), which were determined by using the method measuring particle size distributions defined in Example 4.

Examples C2 to C11

The substantially same process as Example C1 was done by changing the concentration of ethanol used as a water-containing alcohol solvent from 0% to 100% to prepare a cubic-shaped crystal of the active ingredient. The weight of the resulting the crystal of the active ingredient (dried weight), the yield per 10.8 g of the starting material, and the particle size distribution of the resulting formulations which was measured according to the method of Example 4 are shown in Table 8.

Meanwhile, a water solution of 0.7% (w/v) disodium hydrogenphosphate (anhydride)/1% (w/v) polysorbate 80 was sterilely filtered through Millipak™ 60 (pore diameter=0.22 µm) to prepare 5200 g of a crystallizing agent.

To a 10 L glass vessel [φ 220 mm×430 mm, caliber φ 95 mm, IWAKI; with a teflon stirring bar for magnetic stirrer (φ 27 mm×108 mm)] whose inside is sterilized, 5000 g of the crystallizing agent was injected. Then, at a crystallizing temperature of around 25° C., the solution of the active ingredient was added dropwise to the glass vessel at a flow rate of 500 mL/min for 10 minutes while stirring the reaction with a magnetic stirrer (model BS -190N, IWAKI) at a stirring speed of 600 rpm to give a crystal slurry of the active ingredient. The crystal in the slurry was a cubic-shaped crystal which was a free form of Compound 1.

The crystal slurry was injected to a SUS316 pressurized filter system (model SF-145, ADVANTEC) to be filtered through a supported PTFE membrane filter pre-attached to the filter system (model: 13110014, pore diameter=1 µm, ADVANTEC), then the crystal of the active ingredient was collected on the filter, and the liquid ingredients were removed.

To the crystal of the active ingredient which was collected on the filter, a sterilely-filtered vehicle solution (about pH 7) comprising 0.14% (w/v) sodium dihydrogenphosphate (dihydrate)/0.26 (w/v) disodium hydrogenphosphate (anhydride)/0.70 (w/v) sodium chloride/0.005% (w/v) polysorbate 80 was injected, and then the mixture was re-suspended, and filtered. After repeating this procedure several times, the vehicle solution was injected thereto again to prepare the desired formulation. The injection volume of the vehicle

TABLE 8

| Example No. | Concentration of ethanol in the solution of the active ingredient (%) | Weight of the precipitated crystal (yield)/g | Yield per the starting material/% | Particle size distribution (D10)/µm | Particle size distribution (D50; mean particle size)/µm | Particle size distribution (D90)/µm |
| --- | --- | --- | --- | --- | --- | --- |
| C2 | 0 | 1.48 | 13.7 | 0.8 | 3.5 | 6.6 |
| C3 | 10 | 1.62 | 15.0 | 2.3 | 5.6 | 10.9 |
| C4 | 20 | 2.16 | 20.0 | 3.9 | 8.8 | 17.9 |
| C5 | 30 | 3.42 | 31.7 | 3.3 | 7.4 | 12.1 |
| C6 | 40 | 6.27 | 58.1 | 5.6 | 8.4 | 13.0 |
| C7 | 50 | 9.63 | 89.2 | 6.0 | 8.7 | 12.7 |
| C8 | 60 | 10.38 | 96.1 | 5.6 | 9.4 | 17.5 |
| C1 | 70 | 10.51 | 97.3 | 5.5 | 10.5 | 18.9 |
| C9 | 80 | 10.12 | 93.7 | 6.6 | 13.0 | 21.1 |
| C10 | 90 | 6.03 | 55.8 | 5.4 | 10.9 | 19.4 |
| C11 | 100 | 1.14 | 10.6 | 5.0 | 12.5 | 24.1 |

Based on the above-listed results of each particle size of the prepared cubic crystal and each yield, the content of an organic solvent in the mixture of an organic solvent and water to prepare the solution of the active ingredient was preferably 40 to 90%, more preferably 60 to 80%. In particular, aqueous 70% ethanol solution was the most preferred.

Example D1

To an aqueous 70% ethanol solution containing 1% (w/v) polysorbate 80, Compound 1 was dissolved so that the concentration of Compound 1 should be 2% (w/v), and then the solution was sterilely filtered through Millipak™ 60 (pore diameter=0.22 µm) to prepare 5200 mL of a solution of the active ingredient.

solution was decided according to "300 mg/mL" in Table 1 so that each ingredient could be adapted to the amount calculated based on its density to prepare 300 mg/mL sustained-release formulation for injection defined in Table 1. The particle size distribution was 9.0 µm (D10), 18.3 µm (mean particle size D50) and 30.6 µm (D90), which were determined by using the method measuring particle size distributions defined in Example 4.

In addition, the volume of the vehicle solution can be adjusted to prepare a formulation of the active ingredient in any concentration besides 300 mg/mL (50, 100, 150, 200, 250, 400, 500, 600 mg/mL, etc.)[Example D1a].

Examples D2-D9

The substantially same process as Example D1 was done by using the crystal of the active ingredient prepared in Example D1 and changing the concentration of polysorbate 80 used in the vehicle solution from 0.01% (w/v) to 0.10% (w/v) to prepare a sustained release formulation for injection which contains 300 mg/mL cubic-shaped crystal of the active ingredient [Examples D2-D5]. The particle size distribution of the resulting formulations which was measured according to the method of Example 4 is shown in Table 9.

Likewise, the substantially same process as Example D1 was done by changing the concentration of polysorbate 80 used in the vehicle solution from 0.5% (w/v) to 2.0% (w/v) to prepare a sustained release formulation for injection which contains a cubic-shaped crystal of the active ingredient [Examples D6-D9; Table 10].

In addition, the volume of the vehicle solution can be adjusted to prepare a formulation of the active ingredient in any concentration besides 300 mg/mL (50, 100, 150, 200, 250, 400, 500, 600 mg/mL, etc.)(Examples D2a-D9a; Table 11).

TABLE 9

| Example No. | Concentration of polysorbate 80 in the vehicle solution (% (w/v)) | Concentration of the active ingredient (mg/mL) | Particle size distribution (D10)/μm | Particle size distribution (D50; mean particle size)/μm | Particle size distribution (D90)/μm |
|---|---|---|---|---|---|
| D1 | 0.005 | 300 | 9.0 | 18.3 | 30.6 |
| D2 | 0.01 | 300 | 8.4 | 17.6 | 29.5 |
| D3 | 0.02 | 300 | 7.3 | 13.8 | 23.4 |
| D4 | 0.05 | 300 | 7.5 | 13.5 | 20.1 |
| D5 | 0.10 | 300 | 7.2 | 12.1 | 20.4 |

TABLE 10

| Example No. | Concentration of polysorbate 80 in the vehicle solution (% (w/v)) | Concentration of the active ingredient (mg/mL) |
|---|---|---|
| D6 | 0.5 | 300 |
| D7 | 1.0 | 300 |
| D8 | 1.5 | 300 |
| D9 | 2.0 | 300 |

TABLE 11

| Example No. | Concentration of polysorbate 80 in the vehicle solution (% (w/v)) | Concentration of the active ingredient (mg/mL) |
|---|---|---|
| D1a | 0.005 | 50, 100, 150, 200, 250, 400, 500, 600, etc. |
| D2a | 0.01 | 50, 100, 150, 200, 250, 400, 500, 600, etc. |
| D3a | 0.02 | 50, 100, 150, 200, 250, 400, 500, 600, etc. |
| D4a | 0.05 | 50, 100, 150, 200, 250, 400, 500, 600, etc. |
| D5a | 0.10 | 50, 100, 150, 200, 250, 400, 500, 600, etc. |
| D6a | 0.5 | 50, 100, 150, 200, 250, 400, 500, 600, etc. |
| D7a | 1.0 | 50, 100, 150, 200, 250, 400, 500, 600, etc. |
| D8a | 1.5 | 50, 100, 150, 200, 250, 400, 500, 600, etc. |
| D9a | 2.0 | 50, 100, 150, 200, 250, 400, 500, 600, etc. |

Example E1

Step (1): To an aqueous 70% ethanol solution containing 1% (w/v) polysorbate 20, Compound 1 was dissolved so that the concentration of Compound 1 should be 2% (w/v), and then the solution was sterilely filtered through SFCA Bottle Top Filter™ (pore diameter=0.22 μm) to prepare 120 mL of a solution of the active ingredient.

Step (2): Meanwhile, a water solution of 0.7% (w/v) disodium hydrogenphosphate (anhydride)/1% (w/v) polysorbate 20 was sterilely filtered through SFCA Bottle Top Filter™ (pore diameter=0.22 μm) to prepare 120 mL of a crystallizing agent.

Step (3): To a 100 mL vial container with a scale attachment [model: WT-110, NICHIDEN-RIKA GLASS; with a teflon stirring bar (φ 8 mm×35 mm)], 50 mL of the crystallizing agent was injected. Then, at a crystallizing temperature of around 25° C., the solution of the active ingredient was added dropwise into the glass bottle at a flow rate of 5 mL/min for 10 minutes while stirring the reaction with a magnetic stirrer (model BS-56L-1, IWAKI) at a stirring speed of 1200 rpm to give a crystal slurry of the active ingredient. The crystal in the slurry was a cubic-shaped crystal which was a free form of Compound 1.

Step (4): The crystal slurry was injected to a reduced-pressure-type glass filter system (index No. XX1504700, MILLIPORE) to be filtered through Omnipore™ membrane filter pre-attached to the filter system (model: JAWP, pore diameter=1 μm, MILLIPORE), then the crystal of the active ingredient was collected on the filter, and the liquid ingredients were removed.

Step (5): To the crystal of the active ingredient which was collected on the filter, a sterilely-filtered vehicle solution (about pH 7) comprising 0.14% (w/v) sodium dihydrogenphosphate (dihydrate)/0.26% (w/v) disodium hydrogenphosphate (anhydride)/0.70 (w/v) sodium chloride/0.20% (w/v) polysorbate 80 was injected, and then the mixture was re-suspended, and filtered. After repeating this procedure several times, the vehicle solution was injected thereto again to prepare the desired formulation. A sustained-release formulation for injection containing 200 mg/mL the active ingredient was prepared by adjusting the volume of the vehicle solution. The particle size distribution was 7.5 μm (D10), 9.8 μm (mean particle size D50) and 13.1 μm (D90), which were determined by using the method measuring particle size distributions defined in Example 4.

In addition, the volume of the vehicle solution can be adjusted to prepare a formulation of the active ingredient in any concentration besides 200 mg/mL (50, 100, 150, 250, 300, 400, 500, 600 mg/mL, etc.) [Example E1a].

Furthermore, the polysorbate 80 contained in the vehicle solution can be replaced with polysorbate 20 and the volume of the vehicle solution can be adjusted to prepare a formulation of the active ingredient in any concentration (50, 100, 150, 200, 250, 300, 400, 500, 600 mg/mL, etc.) [Example E1b].

Examples E2-E8

The surfactant (polysorbate 20) used in the solution of the active ingredient (Step (1)) and the crystallizing agent (Step (2)) in Example E1 were replaced with any other surfactant in the same concentration such as polyoxyethylene hydrogenated castor oil 50 [Example E2], polyoxyethylene hydrogenated castor oil 60 [Example E3], poloxamer 188 [Example E4], polyoxyethylene castor oil [Example E5], benzalkonium chloride [Example E6], sodium lauryl sulfate

[Example E7], and additive-free (0%) [Example E8], and then the substantially same process as Example E1 was done to prepare a sustained release formulation for injection which contains 200 mg/mL cubic-shaped crystal of the active ingredient. The surfactant used in each example and the particle size distribution of the resulting formulations which was measured according to the method of Example 4 are shown in Table 12.

In addition, the volume of the vehicle solution can be adjusted to prepare a formulation of the active ingredient in any concentration besides 200 mg/mL (50, 100, 150, 250, 300, 400, 500, 600 mg/mL, etc.)(Table 13).

In addition, the polysorbate 80 used in the vehicle solution (Step (5)) in Example E1 was replaced with any other surfactant in the same concentration such as polyoxyethylene hydrogenated castor oil 50 [Example E2b], polyoxyethylene hydrogenated castor oil 60 [Example E3b], poloxamer 188 [Example E4b], polyoxyethylene castor oil [Example E5b], benzalkonium chloride [Example E6b], and sodium lauryl sulfate [Example E7b], and then the substantially same process as Step (5) in Example E1 was done adjusting the volume of the vehicle solution to prepare a formulation which contains a cubic-shaped crystal of the active ingredient in any concentration (50, 100, 150, 200, 250, 300, 400, 500, 600 mg/mL, etc.) (Table 14).

TABLE 12

| Example No. | Surfactant in the solution of the active ingredient and crystallizing agent (each 1% (w/v). | Surfactant in the vehicle solution in Step (5) (each 0.2% (w/v)) | Concentration of the active ingredient (mg/mL) | Particle size distribution (D10)/μm | Particle size distribution (D50; mean particle size)/μm | Particle size distribution (D90)/μm |
|---|---|---|---|---|---|---|
| E1 | polysorbate 20 | polysorbate 80 | 200 | 7.5 | 9.8 | 13.1 |
| E2 | polyoxyethylene hydrogenated castor oil 50 | polysorbate 80 | 200 | 11.9 | 15.1 | 19.5 |
| E3 | polyoxyethylene hydrogenated castor oil 60 | polysorbate 80 | 200 | 9.8 | 12.3 | 15.7 |
| E4 | poloxamer 188 | polysorbate 80 | 200 | 8.1 | 15.1 | 24.8 |
| E5 | polyoxyethylene castor oil | polysorbate 80 | 200 | 7.9 | 13.7 | 19.2 |
| E6 | benzalkonium chloride | polysorbate 80 | 200 | 9.2 | 12.9 | 19.0 |
| E7 | sodium lauryl sulfate | polysorbate 80 | 200 | 10.0 | 15.3 | 21.0 |
| E8 | additive-free (0%) | polysorbate 80 | 200 | 53.1 | 180.6 | 284.4 |

TABLE 13

| Example No. | Surfactant in the solution of the active ingredient and crystallizing agent (each 1% (w/v)) | Surfactant in the vehicle solution in Step (5) (each 0.2% (w/v)) | Concentration of the active ingredient (mg/mL) |
|---|---|---|---|
| E1a | polysorbate 20 | polysorbate 80 | 50, 100, 150, 250, 300, 400, 500, 600, etc. |
| E2a | polyoxyethylene hydrogenated castor oil 50 | polysorbate 80 | 50, 100, 150, 250, 300, 400, 500, 600, etc. |
| E3a | polyoxyethylene hydrogenated castor oil 60 | polysorbate 80 | 50, 100, 150, 250, 300, 400, 500, 600, etc. |
| E4a | poloxamer 188 | polysorbate 80 | 50, 100, 150, 250, 300, 400, 500, 600, etc. |
| E5a | polyoxyethylene castor oil | polysorbate 80 | 50, 100, 150, 250, 300, 400, 500, 600, etc. |
| E6a | benzalkonium chloride | polysorbate 80 | 50, 100, 150, 250, 300, 400, 500, 600, etc. |
| E7a | sodium lauryl sulfate | polysorbate 80 | 50, 100, 150, 250, 300, 400, 500, 600, etc. |

TABLE 14

| Example No. | Surfactant in the solution of the active ingredient and crystallizing agent (each 1% (w/v)) | Surfactant in the vehicle solution in Step (5) (each 0.2% (w/v)) | Concentration of the active ingredient (mg/mL) |
|---|---|---|---|
| E1b | polysorbate 20 | polysorbate 20 | 50, 100, 150, 200, 250, 300, 400, 500, 600, etc. |
| E2b | polyoxyethylene hydrogenated castor oil 50 | polyoxyethylene hydrogenated castor oil 50 | 50, 100, 150, 200, 250, 300, 400, 500, 600, etc. |
| E3b | polyoxyethylene hydrogenated castor oil 60 | polyoxyethylene hydrogenated castor oil 60 | 50, 100, 150, 200, 250, 300, 400, 500, 600, etc. |
| E4b | poloxamer 188 | poloxamer 188 | 50, 100, 150, 200, 250, 300, 400, 500, 600, etc. |

TABLE 14-continued

| Example No. | Surfactant in the solution of the active ingredient and crystallizing agent (each 1% (w/v) | Surfactant in the vehicle solution in Step (5) (each 0.2% (w/v) | Concentration of the active ingredient (mg/mL) |
|---|---|---|---|
| E5b | polyoxyethylene castor oil | polyoxyethylene castor oil | 50, 100, 150, 200, 250, 300, 400, 500, 600, etc. |
| E6b | benzalkonium chloride | benzalkonium chloride | 50, 100, 150, 200, 250, 300, 400, 500, 600, etc. |
| E7b | sodium lauryl sulfate | sodium lauryl sulfate | 50, 100, 150, 200, 250, 300, 400, 500, 600, etc. |

Example F1

To an aqueous 70% ethanol solution containing 1% (w/v) polysorbate 80, Compound 1 was dissolved so that the concentration of Compound 1 should be 2% (w/v), and then the solution was sterilely filtered through SFCA Bottle Top Filter™ (pore diameter=0.22 μm) to prepare 500 mL of a solution of the active ingredient.

Meanwhile, a water solution of 50 mmol/L dipotassium hydrogenphosphate/1% (w/v) polysorbate 80 was sterilely filtered through SFCA Bottle Top Filter™ (pore diameter=0.22 μm) to prepare 500 g of a crystallizing agent.

To a 100 mL vial container with a scale attachment [model: WT-110, NICHIDEN-RIKA GLASS; with a teflon stirring bar (φ 8 mm×35 mm)], 50 mL of the crystallizing agent was injected. Then, at a crystallizing temperature of around 25° C., the solution of the active ingredient was added dropwise into the glass bottle at a flow rate of 5 mL/min for 10 minutes while stirring the reaction with a magnetic stirrer (model BS-56L-1, IWAKI) at a stirring speed of 1200 rpm to give a crystal slurry of the active ingredient. The crystal in the slurry was a cubic-shaped crystal which was a free form of Compound 1.

The crystal slurry was injected to a reduced-pressure-type glass filter system (index No. XX1504700, MILLIPORE) to be filtered through Omnipore™ membrane filter pre-attached to the filter system (model: JAWP, pore diameter=1 μm, MILLIPORE), then the crystal of the active ingredient was collected on the filter, and the liquid ingredients were removed.

To the crystal of the active ingredient which was collected on the filter, a sterilely-filtered vehicle solution (about pH 7) comprising 0.14% (w/v) sodium dihydrogenphosphate (dihydrate)/0.26% (w/v) disodium hydrogenphosphate (anhydride)/0.70% (w/v) sodium chloride/0.2% (w/v) polysorbate 80 was injected, and then the mixture was re-suspended, and filtered. After repeating this procedure several times, the vehicle solution was injected thereto again to prepare the desired formulation. The injection volume of the vehicle solution was decided according to "200 mg/mL" in Table 1 so that each ingredient could be adapted to the amount calculated based on its density to prepare 200 mg/mL sustained-release formulation for injection defined in Table 1. The particle size distribution was 6.3 μm (D10), 10.2 μm (mean particle size D50), 16.7 μm (D90), which were determined by using the method measuring particle size distributions defined in Example 4.

In addition, the volume of the vehicle solution can be adjusted to prepare a formulation of the active ingredient in any concentration besides 200 mg/mL (50, 100, 150, 250, 300, 400, 500, 600 mg/mL, etc.) [Example F1a].

Furthermore, the 0.14 (w/v) sodium dihydrogenphosphate (dihydrate)/0.26% (w/v) disodium hydrogenphosphate (anhydride) contained in the vehicle solution can be replaced with potassium dihydrogenphosphate/dipotassium hydrogen phosphate in order to adjust pH to around 7, and the volume of the vehicle solution can be adjusted to prepare a formulation of the active ingredient in any concentration (50, 100, 150, 200, 250, 300, 400, 500, 600 mg/mL, etc.) [Example F1b].

Examples F2-F8

The 50 mmol/L dipotassium hydrogen phosphate (buffer) used in the crystallizing agent in Example F1 was replaced with any other buffer in the same mole concentration (mol/L) or a pH regulator such as arginine [Example F2], trometamol [Example F3], sodium carbonate [Example F4], triethanolamine [Example F5], meglumine [Example F6], sodium hydroxide [Example F7], and disodium hydrogenphosphate [Example F8]) and then the substantially same process as Example F1 was done to prepare a sustained release formulation for injection which contains 200 mg/mL cubic-shaped crystal of the active ingredient. The buffer used in each example and the particle size distribution of the resulting formulations which was measured according to the method of Example 4 are shown in Table 15.

In addition, the volume of the vehicle solution can be adjusted to prepare a formulation of the active ingredient in any concentration besides 200 mg/mL (50, 100, 150, 250, 300, 400, 500, 600 mg/mL, etc.) (Table 16).

In addition, the buffer [0.14% (w/v) sodium dihydrogenphosphate (dihydrate)/0.26% (w/v) disodium hydrogenphosphate (anhydride)] used in the vehicle solution in Example F1 was replaced with any other buffer such as L-arginine hydrochloride/L-arginine (pH: about 7) [Example F2b], trometamol (pH: about 7) [Example F3b], sodium hydrogen carbonate/sodium carbonate (pH: about 7) [Example F4b], triethanolamine (pH: about 7) [Example F5b], and meglumine (pH: about 7) [Example F6b]), and then the substantially same process as Example F1 was done adjusting the volume of the vehicle solution to prepare a formulation which contains a cubic-shaped crystal of the active ingredient in any concentration (50, 100, 150, 200, 250, 300, 400, 500, 600 mg/mL, etc.) (Table 17).

TABLE 15

| Example No. | Buffer in the crystallizing agent (each 50 mmol/L) | Buffer in the vehicle solution | Concentration of the active ingredient (mg/mL) | Particle size distribution (D10)/μm | Particle size distribution (D50; mean particle size)/μm | Particle size distribution (D90)/μm |
|---|---|---|---|---|---|---|
| F1 | dipotassium hydrogen phosphate | 0.14% (w/v) sodium dihydrogenphosphate (dihydrate)/0.26% (w/v) disodium hydrogenphosphate (anhydride) | 200 | 6.3 | 10.2 | 16.7 |
| F2 | arginine | same as above | 200 | 8.1 | 10.2 | 13.4 |
| F3 | trometamol | same as above | 200 | 7.1 | 10.5 | 19.4 |
| F4 | sodium carbonate | same as above | 200 | 7.2 | 9.6 | 14.8 |
| F5 | triethanolamine | same as above | 200 | 8.0 | 10.5 | 14.8 |
| F6 | meglumine | same as above | 200 | 6.7 | 9.0 | 15.8 |
| F7 | sodium hydroxide | same as above | 200 | 19.2 | 25.6 | 33.4 |
| F8 | disodium hydrogenphosphate | same as above | 200 | 6.3 | 10.2 | 16.7 |

TABLE 16

| Example No. | Buffer in the crystallizing agent (each 50 mmol/L) | Buffer in the vehicle solution | Concentration of the active ingredient (mg/mL) |
|---|---|---|---|
| F1a | dipotassium hydrogen phosphate | 0.14% (w/v) sodium dihydrogenphosphate (dihydrate)/0.26% (w/v) disodium hydrogenphosphate (anhydride) | 50, 100, 150, 250, 300, 400, 500, 600, etc. |
| F2a | arginine | same as above | 50, 100, 150, 250, 300, 400, 500, 600, etc. |
| F3a | trometamol | same as above | 50, 100, 150, 250, 300, 400, 500, 600, etc. |
| F4a | sodium carbonate | same as above | 50, 100, 150, 250, 300, 400, 500, 600, etc. |
| F5a | triethanolamine | same as above | 50, 100, 150, 250, 300, 400, 500, 600, etc. |
| F6a | meglumine | same as above | 50, 100, 150, 250, 300, 400, 500, 600, etc. |
| F7a | sodium hydroxide | same as above | 50, 100, 150, 250, 300, 400, 500, 600, etc. |
| F8a | disodium hydrogenphosphate | same as above | 50, 100, 150, 250, 300, 400, 500, 600, etc. |

TABLE 17

| Example No. | Buffer in the crystallizing agent (each 50 mmol/L) | Buffer in the vehicle solution | Concentration of the active ingredient (mg/mL) |
|---|---|---|---|
| F1b | dipotassium hydrogen phosphate | potassium dihydrogenphosphate/dipotassium hydrogen phosphate (pH about 7) | 50, 100, 150, 200, 250, 300, 400, 500, 600, etc. |
| F2b | arginine | L-arginine hydrochloride/L-arginine (pH about 7) | 50, 100, 150, 200, 250, 300, 400, 500, 600, etc. |
| F3b | trometamol | trometamol (pH about 7) | 50, 100, 150, 200, 250, 300, 400, 500, 600, etc. |
| F4b | sodium carbonate | sodium hydrogen carbonate/sodium carbonate (pH about 7) | 50, 100, 150, 200, 250, 300, 400, 500, 600, etc. |
| F5b | triethanolamine | triethanolamine (pH about 7) | 50, 100, 150, 200, 250, 300, 400, 500, 600, etc. |
| F6b | meglumine | meglumine (pH about 7) | 50, 100, 150, 200, 250, 300, 400, 500, 600, etc. |

Examples F9 to F16

The 0.70% (w/v) sodium chloride (isotonic agent) used in the vehicle solution in Example F1 can be replaced with any other isotonic agent such as D-mannitol [about 5% (w/v); Example F9], D-fructose [about 5% (w/v); Example F10], D-xylitol [about 5% (w/v); Example F11], D-sorbitol [about 5% (w/v); Example F12], D-lactose [about 10% (w/v); Example F13], D-glucose [about 5% (w/v); Example F14], D-trehalose [about 10% (w/v); Example F15], and D-sucrose [about 10% (w/v); Example F16] and D-maltose [about 5% (w/v); Example F17]) to prepare a sustained release formulation for injection of the present invention. The volume of the vehicle solution can be adjusted to prepare a formulation of the active ingredient in any concentration (50, 100, 150, 200, 250, 300, 400, 500, 600 mg/mL, etc.) (Table 18).

TABLE 18

| Example No. | Isotonic agent in the vehicle solution | Concentration of isotonic agent (per the vehicle solution) % (w/v) | Concentration of the active ingredient (mg/mL) |
|---|---|---|---|
| F1 | sodium chloride | 0.70 | 50, 100, 150, 200, 250, 300, 400, 500, 600, etc. |
| F9 | D-mannitol | about 5 | 50, 100, 150, 200, 250, 300, 400, 500, 600, etc. |
| F10 | D-fructose | about 5 | 50, 100, 150, 200, 250, 300, 400, 500, 600, etc. |
| F11 | D-xylitol | about 5 | 50, 100, 150, 200, 250, 300, 400, 500, 600, etc. |
| F12 | D-sorbitol | about 5 | 50, 100, 150, 200, 250, 300, 400, 500, 600, etc. |
| F13 | D-lactose | about 10 | 50, 100, 150, 200, 250, 300, 400, 500, 600, etc. |
| F14 | D-glucose | about 5 | 50, 100, 150, 200, 250, 300, 400, 500, 600, etc. |
| F15 | D-trehalose | about 10 | 50, 100, 150, 200, 250, 300, 400, 500, 600, etc. |
| F16 | D-sucrose | about 10 | 50, 100, 150, 200, 250, 300, 400, 500, 600, etc. |
| F17 | D-maltose | about 10 | 50, 100, 150, 200, 250, 300, 400, 500, 600, etc. |

Example F18

Lidocaine hydrochloride [about 0.5% (w/v)-2% (w/v)] can be additionally contained in the vehicle solution prepared in Example F8 and the volume of the vehicle solution can be adjusted to prepare a formulation of lidocaine hydrochloride in any concentration (50, 100, 150, 200, 250, 300, 400, 500, 600 mg/mL, etc.).

Example F19

Lidocaine hydrochloride described in Example F18 can be replaced with procaine hydrochloride [about 0.5% (w/v)-2% (w/v)] and the volume of the vehicle solution can be adjusted to prepare a formulation of procaine hydrochloride in any concentration (50, 100, 150, 200, 250, 300, 400, 500, 600 mg/mL, etc.).

Example F20

Lidocaine hydrochloride described in Example F18 can be replaced with meprylcaine hydrochloride [about 1% (w/v)-3% (w/v)] and the volume of the vehicle solution can be adjusted to prepare a formulation of meprylcaine hydrochloride in any concentration (50, 100, 150, 200, 250, 300, 400, 500, 600 mg/mL, etc.).

Example G1

Effect of Solvent in Solution of the Active Ingredient

To an aqueous 70% methanol solution containing 1% (w/v) polysorbate 80, Compound 1 was dissolved so that the concentration of Compound 1 should be 2% (w/v), and then the solution was sterilely filtered through SFCA Bottle Top Filter™ (pore diameter=0.22 μm) to prepare 120 mL of a solution of the active ingredient.

Meanwhile, a water solution of 0.7% (w/v) disodium hydrogenphosphate (anhydride)/1% (w/v) polysorbate 20 was sterilely filtered through SFCA Bottle Top Filter™ (pore diameter=0.22 μm) to prepare 120 mL of a crystallizing agent.

To a 100 mL vial container with a scale attachment [model: WT-110, NICHIDEN-RIKA GLASS; with a teflon stirring bar (φ 8 mm×35 mm)], 50 mL of the crystallizing agent was injected. Then, at a crystallizing temperature of around 25° C., the solution of the active ingredient was added dropwise into the glass bottle at a flow rate of 5 mL/min for 10 minutes while stirring the reaction with a magnetic stirrer (model BS-56L-1, IWAKI) at a stirring speed of 1200 rpm to give a crystal slurry of the active ingredient. The crystal in the slurry was a cubic-shaped crystal which was a free form of Compound 1.

The crystal slurry was injected to a reduced-pressure-type glass filter system (index No. XX1504700, MILLIPORE) to be filtered through Omnipore™ membrane filter pre-attached to the filter system (model: JAWP, pore diameter=1 μm, MILLIPORE), then the crystal of the active ingredient was collected on the filter, and the liquid ingredients were removed.

To the crystal of the active ingredient which was collected on the filter, a sterilely-filtered vehicle solution (about pH 7) comprising 0.14% (w/v) sodium dihydrogenphosphate (dihydrate)/0.26% (w/v) disodium hydrogenphosphate (anhydride)/5.0% (w/v) D-mannitol/0.2% (w/v) polysorbate 80 was injected, and then the mixture was re-suspended, and filtered. After repeating this procedure several times, the vehicle solution was injected thereto again to prepare the desired formulation. The injection volume of the vehicle solution was decided according to "200 mg/mL" in Table 1 so that each ingredient could be adapted to the amount calculated based on its density to prepare 200 mg/mL sustained-release formulation for injection defined in Table 1. The particle size distribution was 5.5 μm (D10), 7.4 μm (mean particle size D50), 9.4 μm (D90), which were determined by using the method measuring particle size distributions defined in Example 4. In addition, the volume of the vehicle solution can be adjusted to prepare a formulation of the active ingredient in any concentration besides 200 mg/mL (50, 100, 150, 250, 300, 400, 500, 600 mg/mL, etc.) [Example G1a].

Examples G2 to G6

The methanol used in the solution of the active ingredient in Example G1 was replaced with any other organic solvent such as acetone [Example G2], N,N-dimethylacetamide [Example G3], 1-propanol [Example G4], 2-propanol [Example G5], and dimethylsulfoxide [Example G6]) and then the substantially same process as Example G1 was done to prepare a sustained release formulation for injection which contains 200 mg/mL cubic-shaped crystal of the active ingredient. The solvent used in each example and the particle size distribution of the resulting formulations which was measured according to the method of Example 4 are shown in Table 19.

In addition, the volume of the vehicle solution can be adjusted to prepare a formulation of the active ingredient in any concentration besides 200 mg/mL (50, 100, 150, 250, 300, 400, 500, 600 mg/mL, etc.) (Table 20).

TABLE 19

| Example No. | Organic solvent in the solution of the active ingredient (concentration: 70%) | Concentration of the active ingredient (mg/mL) | Particle size distribution (D10)/μm | Particle size distribution (D50; mean particle size)/μm | Particle size distribution (D90)/μm |
|---|---|---|---|---|---|
| G1 | methanol | 200 | 5.5 | 7.4 | 9.4 |
| G2 | acetone | 200 | 8.4 | 15.1 | 21.4 |
| G3 | N,N-dimethyl-acetamide | 200 | 4.1 | 8.8 | 18.9 |
| G4 | 1-propanol | 200 | 10.5 | 18.4 | 25.9 |
| G5 | 2-propanol | 200 | 4.8 | 10.3 | 25.2 |
| G6 | dimethyl-sulfoxide | 200 | 5.3 | 10.8 | 16.9 |

TABLE 20

| Example No. | Organic solvent in the solution of the active ingredient (concentration: 70%) | Concentration of the active ingredient (mg/mL) |
|---|---|---|
| G1a | methanol | 50, 100, 150, 250, 300, 400, 500, 600, etc. |
| G2a | acetone | 50, 100, 150, 250, 300, 400, 500, 600, etc. |
| G3a | N,N-dimethylacetamide | 50, 100, 150, 250, 300, 400, 500, 600, etc. |
| G4a | 1-propanol | 50, 100, 150, 250, 300, 400, 500, 600, etc. |
| G5a | 2-propanol | 50, 100, 150, 250, 300, 400, 500, 600, etc. |
| G6a | dimethylsulfoxide | 50, 100, 150, 250, 300, 400, 500, 600, etc. |

Example 12

Effect of Mean Particle Size (1)

(Measurement of Particle Size Distribution)

Table 21 shows the formulation composition of Formulations No. 4 to No. 6, wherein all of the formulations have 200 mg/mL of the active ingredient.

Table 22 shows the obtained particle size distributions (D10, D50, D90) of Formulations No. 4 to 6 which were determined by the measurement method of particle size distribution described in Example 4. The mean particle sizes were 5.0 μm (Formulation No. 4), 11.3 μm (Formulation No. 5), and 25.8 μm (Formulation No. 6).

TABLE 21

| Formulation composition | |
|---|---|
| Active ingredient (free form of Compound 1) | 200 mg |
| Polysorbate 80 | 1.7 mg |
| Sodium dihydrogenphosphate dihydrate | 1.2 mg |
| Disodium hydrogenphosphate anhydride | 2.2 mg |
| Sodium chloride | 5.8 mg |
| Water for injection | 1 mL (total volume) |

TABLE 22

| Example | Formulation No. | Particle size distribution (μm) | | |
|---|---|---|---|---|
| | | D10 | Mean particle size D50 | D90 |
| 6 | 4 | 0.5 | 5.0 | 7.9 |
| 7 | 5 | 6.3 | 11.3 | 17.5 |
| 8 | 6 | 17.5 | 25.8 | 35.0 |

(Animal Experiments)

Figure 2:
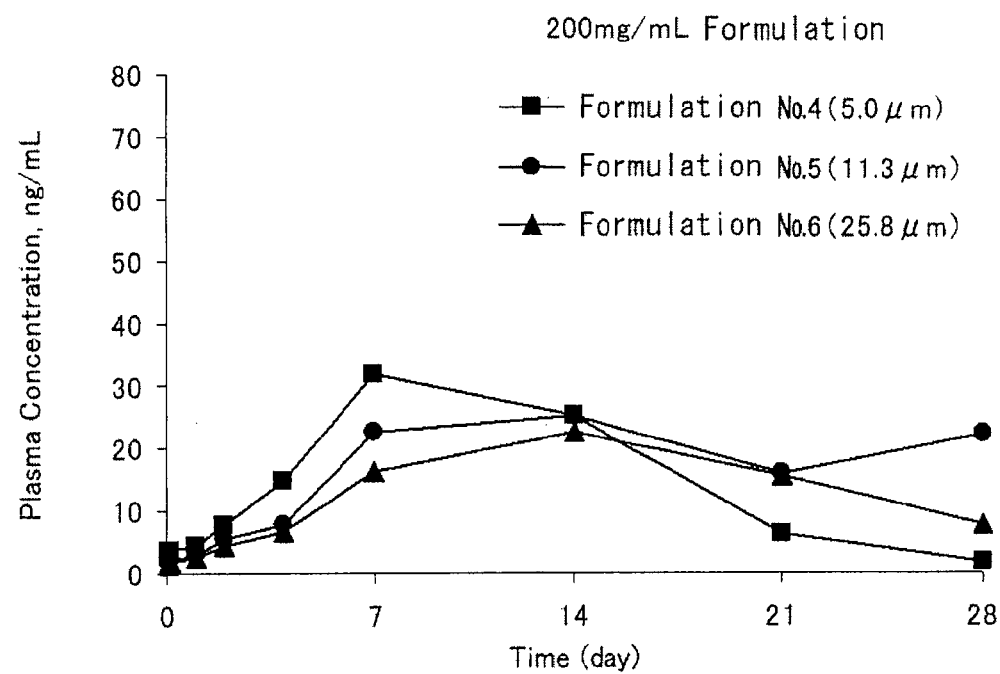
FIG. 2 is a graph showing a transition of the average concentration of drug in the plasma when the formulation prepared in Example 12 (200 mg/mL) was administered to rats in a dose of 50 mg/kg.

Each of the formulations having 200 mg/mL of the active ingredient (i.e. Formulations No. 4 to No. 6) was administered to gastrocnemius muscle of six rats [Sprague-Dawley rats (SD), male, 9 weeks old, 250-300 g] in a dose of 50 mg/kg (0.25 mL/kg). The blood was collected 1, 2, and 4 hours, 1, 2, 4, 7, 14, 21, and 28 days after the administration, and the results showed that the blood level of the present compound held up well. As shown in FIG. 2, in case that the mean particle size was 5.0 μm (Formulation No. 4), the present compound rapidly disappeared from the blood after 7 days (1 week); whereas in case that the mean particle size was 11.3 μm (Formulation No. 5) and 25.8 μm (Formulation No. 6), the blood level of the present compound held up well for at least 14 days (2 weeks).

Example 13

Effect of Mean Particle Size (2)

Table 23 shows the formulation composition of Formulations No. 7 to No. 10, wherein all of the formulations have 400 mg/mL of the active ingredient.

Table 24 shows the obtained particle size distributions (D10, D50, D90) of Formulations No. 7 to 10 which were determined by the measurement method of particle size distribution described in Example 4. The mean particle sizes were 4.8 μm (Formulation No. 7), 11.1 μm (Formulation No. 8), 20.0 μm (Formulation No. 9), and 11.7 μm (Formulation No. 10).

TABLE 23

| Formulation composition | |
|---|---|
| Active ingredient (free form of Compound 1) | 400 mg |
| Polysorbate 80 | 1.3 mg |
| Sodium dihydrogenphosphate dihydrate | 0.9 mg |
| Disodium hydrogenphosphate anhydride | 1.7 mg |

TABLE 23-continued

Formulation composition

| Sodium chloride | 4.6 mg |
|---|---|
| Water for injection | 1 mL (total volume) |

TABLE 24

| Example | Formulation No. | Particle size distribution (μm) | | |
|---|---|---|---|---|
| | | Mean particle size | | |
| | | D10 | D50 | D90 |
| 6 | 7 | 0.4 | 4.8 | 7.8 |
| 7 | 8 | 5.9 | 11.1 | 17.5 |
| 9 | 9 | 13.6 | 20.0 | 28.2 |
| 10 | 10 | 0.5 | 11.7 | 34.1 |

(Animal Experiments)

Figure 3:
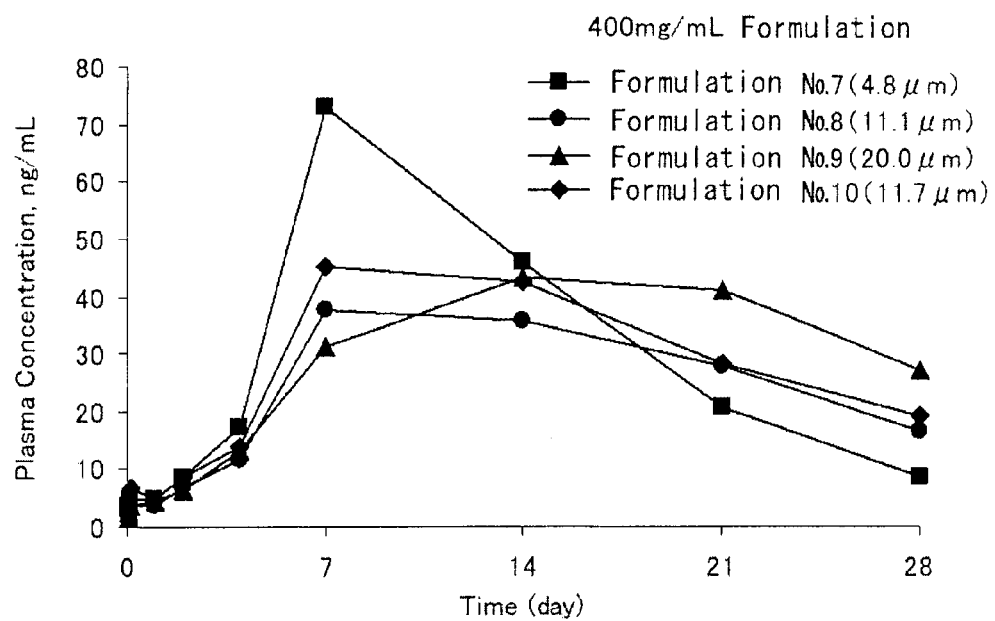
FIG. 3 is a graph showing a transition of the average concentration of drug in the plasma when the formulation prepared in Example 13 (400 mg/mL) was administered to rats in a dose of 100 mg/kg.

Each of the formulations having 400 mg/mL of the active ingredient (i.e. Formulations No. 7 to No. 10) was administered to gastrocnemius muscle of six rats [Sprague-Dawley rats (SD), male, 9 weeks old, 250-300 g] in a dose of 100 mg/Kg (0.25 mL/kg). The blood was collected 1, 2, and 4 hours, 1, 2, 4, 7, 14, 21, and 28 days after the administration, and the results showed that the blood level of the present compound held up well. As shown in FIG. 3, in case that the mean particle size was 4.8 μm (Formulation No. 7), the present compound rapidly disappeared from the blood after 7 days (1 week); whereas in case that the mean particle size was 11.1 μm (Formulation No. 8), 20.0 μm (Formulation No. 9) and 11.7 μm (Formulation No. 10), the blood level of the present compound held up well for at least 14 days (2 weeks).

Example 14

Effect of Mean Particle Size on Needle Passability (1)

Each of the active ingredient crystals having the following mean particle size:
11.1 μm (Formulation No. 1, prepared in Example 1);
15.2 μm (Formulation No. 2, prepared in Example 2);
19.9 μm (Formulation No. 3, prepared in Example 3); and
54.3 μm (Formulation No. 11, prepared in Example 11)
was formulated to three types of formulations having a concentration of 200, 300, and 400 mg/mL. 1 mL of each formulation was put into a 2.5 mL syringe equipped with a 22 gauge needle (the length of the needle=1½, Terumo). As a material for evaluating the needle passability, pork ham and melamine form (AISEN) were selected because these materials are similar to muscles in the point that they require considerable power to insert the needle into the materials. Each formulation was injected into the materials, and then the needle passability was evaluated by judging whether the whole amount of each formulation could be injected or not (i.e. whether the needle's inside is clogged with the crystal or not). The results of pork ham and melamine form are shown in Table 25 and Table 26, respectively. In Table 25 and Table 26, "o" shows that it was possible to inject the whole amount of the formulation into the materials, whereas "x" shows that it was difficult to inject all of them. As a result, there is no difference between pork ham and melamine form when they are used as a material for evaluating the needle passability, and the results also indicate that it would be more difficult to make an injection with the needle when the active ingredients are more concentrated and the mean particle sizes are bigger.

TABLE 25

Injection into pork ham

| Formulation No. | Mean particle size (μm) | Concentration of active ingredient (mg/mL) | | |
|---|---|---|---|---|
| | | 200 | 300 | 400 |
| 1 | 11.1 | o | o | o |
| 2 | 15.2 | o | o | o |
| 3 | 19.9 | o | o | x |
| 11 | 54.3 | o | x | x |

TABLE 26

Injection into melamine form

| Formulation No. | Mean particle size (μm) | Concentration of active ingredient (mg/mL) | | |
|---|---|---|---|---|
| | | 200 | 300 | 400 |
| 1 | 11.1 | o | o | o |
| 2 | 15.2 | o | o | o |
| 3 | 19.9 | o | o | x |
| 11 | 54.3 | o | x | x |

Example 15

Effect of Mean Particle Size on Needle Passability (2)

In order to evaluate the effect of the mean particle size on the needle passability in more detail, formulations of the crystal which have a concentration of 200-400 mg/mL with a 10 mg/mL interval were prepared with the crystals having a mean particle size of 11.1-84.9 μm. 1 mL of each formulation was put into a 2.5 mL syringe equipped with an 18 to 22 gauge needle (the length of the needle=1½, Terumo) or a 23 gauge needle (the length of the needle=1¼, Terumo). Each formulation was injected into the melamine form used in Example 14, and the needle passability was evaluated by judging whether the whole amount of each formulation could be injected or not (i.e. whether the needle's inside is clogged with the crystal or not). Table 27 shows the results of these. In Table 27, "o" shows that it is possible to inject the whole amount of the formulation into the melamine form, whereas "x" shows that it is difficult to inject them, and also the gauge needle is shown in brackets. The results are as follows:

(i) when the mean particle size of the crystal was less than 54.3 μm, the formulations at a concentration of less than 220 mg/mL were able to pass through a needle of 23 gauge;

(ii) when the mean particle size of the crystal was less than 25.2 μm, the formulations at a concentration of less than 260 mg/mL were able to pass through at least a needle of 22 gauge;

(iii) when the mean particle size of the crystal was less than 19.9 μm, the formulations at a concentration of less than 300 mg/mL were able to pass through at least a needle of 22 gauge;

(iv) when the mean particle size of the crystal was less than 17.6 μm, the formulations at a concentration of less than 330 mg/mL were able to pass through at least a needle of 22 gauge; and (v) when the mean particle size of the crystal was less than 15.2 µm, the formulations at a concentration of less than 400 mg/mL were able to pass through at least a needle of 22 gauge.

µm - about 18 µm, about 5 µm - about 16 µm, about 8 µm - about 20 µm, about10 µm - about 26 µm, about 10 µm - about 20 µm, about 10 µm - about 18 µm, or about 10 µm-about 16 µm.

TABLE 27

| Mean particle size (µm) | Concentrations of active ingredient (mg/mL) | | | | | |
|---|---|---|---|---|---|---|
| | 50-190 | 200-220 | 230-260 | 270-300 | 310-330 | 340-400 |
| 11.1 | ○ (18-23G) | ○ (18-23G) | ○ (18-23G) | ○ (18-23G) | ○ (18-23G) | ○ (18-23G) |
| 15.2 | ○ (18-23G) | ○ (18-23G) | ○ (18-23G) | ○ (18-23G) | ○ (18-23G) | ○ (18-22G) |
| 17.6 | ○ (18-23G) | ○ (18-23G) | ○ (18-23G) | ○ (18-23G) | ○ (18-22G) | x (18G) |
| 19.9 | ○ (18-23G) | ○ (18-23G) | ○ (18-23G) | ○ (18-22G) | x (18G) | x (18G) |
| 25.2 | ○ (18-23G) | ○ (18-23G) | ○ (18-22G) | x (18G) | x (18G) | x (18G) |
| 54.3 | ○ (18-23G) | ○ (18-23G) | x (18G) | x (18G) | x (18G) | x (18G) |
| 56.1 | x (18G) | x (18G) | x (18G) | x (18G) | x (18G) | x (18G) |
| 84.9 | x (18G) | x (18G) | x (18G) | x (18G) | x (18G) | x (18G) |

[Industrial Applicability]

The present invention can get more patients effectively treated because the present compound in the present formulation can be continuously released for at least more than 2 to 4 weeks, and the present compound can be also formulated into a sustained release formulation for injection which has a good needle passability.

What is claimed is:

1. A composition comprising the following (1) to (5),
   (1) N-[4-[4-(1,2-benzisothiazol-3-yl)-1-piperazinyl]-(2R, 3R)-2,3-tetramethylene-butyl]-(1'R, 2'S, 3'R, 4'S)-2,3-bicyclo[2,2,1]heptanedicarboximide or a pharmaceutically acceptable acid addition salt thereof as an active ingredient,
   wherein the active ingredient is in crystal form, and the mean particle size of the crystal is about 4 µm - about 26 µm,
   (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil,
   (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid,
   (4) an isotonic agent comprising at least one ingredient selected from the group consisting of sodium chloride and D-mannitol, and
   (5) water for injection.

2. The composition of claim 1 wherein the mean particle size of the crystal is about 4 µm - about 20 µm, about 4 µm - about 18 µm, about 4 µm - about 16 µm, about 5 µm - about 26 µm, about 5 µm - about 20 µm, about 5

3. The composition of claim 1 wherein the crystal is a cubic crystal.

4. The composition of claim 3 wherein the ratio between length and width of the cubic crystal is about 1:1, and the ratio between length and height thereof is about 1:0.8 to about 1:1.2.

5. The composition of claim 1 wherein the active ingredient in crystal form is contained in about 5% (w/v) to about 60% (w/v) per the whole of the composition.

6. The composition of claim 1 wherein the surfactant is polysorbate 80.

7. The composition of claim 1 wherein the surfactant is contained in about 0.005% (w/v) to about 2% (w/v) per the whole of the composition.

8. The composition of claim 1 wherein the buffer is sodium dihydrogenphosphate and/or disodium hydrogenphosphate.

9. The composition of claim 1 wherein the buffer is contained in about 0.01% (w/v) to about 2% (w/v) per the whole of the composition.

10. The composition of claim 1 wherein the isotonic agent is sodium chloride.

11. The composition of claim wherein the isotonic agent is contained in about 0.1% (w/v) to about 10% (w/v) per the whole of the composition.

12. A sustained release formulation for injection which comprises the composition according to claim 1.

13. The formulation of claim 12 wherein the active ingredient is contained in a concentration of about 50 mg/mL to about 600 mg/mL.

14. The formulation of claim 12 wherein the surfactant is contained in a concentration of about 0.05 mg/mL to about 20 mg/mL.

15. The formulation of claim 12 wherein the buffer is contained in a concentration of about 0.1 mg/mL to about 20 mg/mL.

16. The formulation of claim 12 wherein the isotonic agent is contained in a concentration of about 1 mg/mL to about 100 mg/mL.

17. The formulation of claim 12 which contains about 50 mg to about 1200 mg of the active ingredient per a container.

18. The formulation of claim 12 which can pass through a needle of 18 to 23 gauges.

19. The formulation of claim 12 wherein the sustained release formulation for injection is a depot formulation for injection.

20. A process for preparation of a sustained-release sterile formulation of claim 12 comprising the following steps (1) to (5):
- step (1): dissolving a mixture comprising N-[4-[4-(1,2-benzisothiazol-3-yl)-1-piperazinyl]-(2R,3R)-2,3-tetramethylene-butyl]-(1'R, 2'S, 3'R, 4'S)-2,3-bicyclo[2,2,1]-heptanedicarboximide or a pharmaceutically acceptable acid addition salt thereof and a surfactant with an organic solvent or a mixture of an organic solvent and water, and then sterilely-filtering the solution through a sterile filter,
- wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (2): preparing a water solution comprising a surfactant and a buffer, sterilely filtering the water solution through a sterile filter, and then sterilely putting the water solution into a sealed vessel whose inside is sterilized,
- wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (3): sterilely adding the sterile solution prepared in step (1) into the sealed vessel containing the water solution in step (2),
- step (4): collecting a crystal precipitated in step (3) through a filter in the sealed vessel, and
- step (5): preparing a water solution comprising a surfactant, a buffer, an isotonic agent and water for injection, sterilely filtering the water solution through a sterile filter, and then sterilely putting the water solution into the sealed vessel containing the crystal in step (4) and mixing the water solution and the crystal.

21. A process for preparation of a sustained-release formulation of claim 12 comprising the following steps (1) to (5):
- step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient,
- wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (2): preparing a water solution comprising a surfactant and a buffer (i.e. a crystallizing agent),
- wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (3): adding the solution of the active ingredient prepared in step (1) into the crystallizing agent in step (2),
- step (4): collecting a crystal precipitated in step (3) through a filter, and
- step (5): preparing a water solution comprising a surfactant, a buffer, an isotonic agent and water for injection (i.e. a vehicle solution), and then mixing the water solution and the crystal of the active ingredient prepared in step (4) to prepare a suspension formulation.

22. The process of claim 20 or 21 further followed by the following steps (6) to (8):
- step (6): aseptically filling a formulation container with the suspension formulation prepared in step (5) to prepare a filled suspension formulation,
- step (7): sterilizing the filled suspension formulation prepared in step (6) by a process of steaming under pressure, and
- step (8): ultrasonicating the filled suspension formulation prepared in step (7).

23. The process of claim 20 or 21, in step (3) the solution of the active ingredient is added to the crystallizing agent in the vessel for crystallization (or the sealed vessel) while circulating the solution (or the suspension solution), in the vessel for crystallization (or the sealed vessel) via a bypass pathway equipped with a pump which can pressure a solution.

24. The process of claim 23 wherein the pump in the bypass pathway is a roller pump.

25. A process for preparation of a sustained-release formulation of claim 12 comprising the following steps (1) to (5):
- step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient,
- wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (2): preparing a water solution comprising a surfactant and a buffer (i.e. a crystallizing agent) and injecting the water solution into a vessel for crystallization equipped with a stirring system,
- wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate,
- step (3): adding the solution of the active ingredient to the crystallizing agent in the vessel for crystallization while circulating the solution (or the suspension solution) in the vessel for crystallization via a bypass pathway equipped with a pump which (i) is connected to the vessel for crystallization, (ii) can make the solution in the vessel for crystallization circulated, and (iii) can pressure the solution, step (4): collecting a crystal precipitated in the vessel for crystallization from the solution (or the suspension solution) in step (3) through a filter, and step (5): preparing a water solution comprising a surfactant, a buffer, an isotonic agent and water for injection (i.e. a vehicle solution), and then injecting the water solution into the crystal of the active ingredient prepared in step (4) and mixing them to prepare a suspension formulation.

26. A process for preparation of a sustained-release formulation of claim 12 comprising the following steps (4) to (8):

step (4): preparing a vehicle solution comprising a surfactant, a buffer, an isotonic agent and water for injection, step (5): injecting the vehicle solution in step (4) into a crystal of N-[4-[4-(1,2-benzisothiazol-3-yl)-1-piperazinyl]-(2R,3R)-2,3-tetramethylene -butyl]-(1'R,2'S,3'R,4'S)-2,3-bicyclo[2,2,1]heptanedicarboximide and mixing them to prepare a suspension formulation, step (6): aseptically filling a formulation container with the suspension formulation prepared in step (5) to prepare a filled suspension formulation step (7): sterilizing the filled suspension formulation prepared in step (6) by a process of steaming under pressure, and step (8): ultrasonicating the filled suspension formulation prepared in step (7).

27. The process of any one of claims 20, 21, or 25 wherein the organic solvent is a single solvent or a mixture of two or more solvents selected from the group consisting of 1-propanol, methanol, ethanol, 2-propanol, acetone, dimethylsulfoxide and N,N-dimethylacetamide.

28. The process of any one of claim 20, 21, or 25 wherein the solvent used in step (1) is a mixture of an organic solvent and water.

29. The process of claim 28 wherein the mixture solvent is a water-containing alcohol.

30. The process of claim 28 wherein the mixture of an organic solvent and water is a water-containing ethanol and the content of ethanol in the water-containing ethanol is 40% to 90%.

31. The process of any one of claim 20, 21, 25 or 26 wherein each the buffer is independently at least one ingredient selected from the group consisting of sodium dihydrogenphosphate, disodium hydrogenphosphate, potassium dihydrogenphosphate, dipotassium hydrogenphosphate, sodium carbonate, triethanolamine, arginine and meglumine.

32. The process of any one of claim 20, 21, 25 or 26 wherein the isotonic agent is sodium chloride and/or D-mannitol.

33. A sustained release formulation for injection which is prepared through the process of any one of claim 20, 21, 25 or 26.

34. A method for treating psychiatric disease which comprises administering the composition of claim 1.

35. The method of claim 34 wherein the psychiatric disease is schizophrenia.

36. The method of claim 34 wherein the psychiatric disease is bipolar disorder.

37. The method of claim 34 wherein the psychiatric disease is depression.

38. A sustained release formulation of claim 12 which is prepared through a process for preparation of a sustained-release formulation for injection comprising the following steps (1) to (5):

step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient, wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (2): preparing a water solution comprising a surfactant and a buffer (i.e. a crystallizing agent) and injecting the water solution into a vessel for crystallization equipped with a stirring system, wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (3): adding the solution of the active ingredient to the crystallizing agent in the vessel for crystallization while circulating the solution (or the suspension solution) in the vessel for crystallization via a bypass pathway equipped with a pump which (i) is connected to the vessel for crystallization, (ii) can make the solution in the vessel for crystallization circulated, and (iii) can pressure the solution, step (4): collecting a crystal precipitated in the vessel for crystallization from the solution (or the suspension solution) in step (3) through a filter, and step (5): preparing a water solution comprising a surfactant, a buffer, an isotonic agent and water for injection (i,e, a vehicle solution), and then injecting the water solution into the crystal of the active ingredient prepared in step (4) and mixing them to prepare a suspension formulation wherein the formulation comprises a composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient, wherein the active ingredient is in crystal form, the mean particle size of the crystal is about 4 μm-about 26 μm, and the crystal is a cubic crystal, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection.

39. The formulation of claim 38 wherein the solvent used in step (1) is a mixture of an organic solvent and water, wherein the mixture of an organic solvent and water is a water-containing ethanol and the content of ethanol in the water-containing ethanol is 40% to 90%.

40. A sustained release formulation of claim 12 which is prepared through a process for preparation of a sustained-release formulation for injection comprising the following steps (1) to (5):

step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof and a surfactant with an organic solvent or a mixture of an organic solvent and water, and then sterilely-filtering the solution through a sterile filter, wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (2): preparing a water solution comprising a surfactant and a buffer, sterilely filtering the water solution through a sterile filter, and then sterilely putting the water solution into a sealed vessel whose inside is sterilized, wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (3): sterilely adding the sterile solution prepared in step (1) into the sealed vessel containing the water solution in step (2), step (4): collecting a crystal precipitated in step (3) through a filter in the sealed vessel, and step (5): preparing a water solution comprising a surfactant, a buffer, an isotonic agent and water for injection, sterilely filtering the water solution through a sterile filter, and then sterilely putting the water solution into the sealed vessel containing the crystal in step (4) and mixing the water solution and the crystal;

wherein the formulation comprises a composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient, wherein the active ingredient is in crystal form, the mean particle size of the crystal is about 4 μm-about 26 μm, and the crystal is a cubic crystal, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection.

41. A sustained release formulation of claim 12 which is prepared through a process for preparation of a sustained-release formulation for injection comprising the following steps (1) to (5):

step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient, wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (2): preparing a water solution comprising a surfactant and a buffer (i.e. a crystallizing agent), wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (3): adding the solution of the active ingredient prepared in step (1) into the crystallizing agent in step (2), step (4): collecting a crystal precipitated in step (3) through a filter, and step (5): preparing a water solution comprising a surfactant, a buffer, an isotonic agent and water for injection (i.e. a vehicle solution), and then mixing the water solution and the crystal of the active ingredient prepared in step (4) to prepare a suspension formulation;

wherein the formulation comprises a composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient, wherein the active ingredient is in crystal form, the mean particle size of the crystal is about 4 μm-about 26 μm, and the crystal is a cubic crystal, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection.

42. A composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient,
wherein the active ingredient is in crystal form, and the mean particle size of the crystal is about 4 μm-about 26 μm, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection;
wherein the composition is prepared through a process comprising a process of crystallization using a surfactant, which is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate.

43. A composition comprising the following (1) to (5), (1) N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboximide or a pharmaceutically acceptable acid addition salt thereof as an active ingredient,
wherein the active ingredient is in crystal form, and the mean particle size of the crystal is about 4 μm-about 26 μm, (2) a surfactant comprising at least one ingredient selected from the group consisting of polysorbate 80, polysorbate 20, polyoxyethylene hydrogenated castor oil 50, polyoxyethylene hydrogenated castor oil 60, poloxamer 188 and polyoxyethylene castor oil, (3) a buffer comprising at least one ingredient selected from the group consisting of sodium phosphate, disodium hydrogenphosphate, sodium dihydrogenphosphate, potassium phosphate, dipotassium hydrogenphosphate, potassium dihydrogenphosphate, trometamol, sodium carbonate, sodium bicarbonate, meglumine, arginine, triethanolamine and citric acid, (4) an isotonic agent comprising at least one ingredient selected from the group consisting of sodium chloride and D-mannitol, and (5) water for injection;
wherein the composition is prepared through a process comprising the following steps (1) to (5):

step (1): dissolving a mixture comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]-heptanedicarboximide or a pharmaceutically acceptable acid addition salt thereof and a surfactant with an organic solvent or a mixture of an organic solvent and water to prepare a solution of the active ingredient, wherein the surfactant in this step (1) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (2): preparing a water solution comprising a surfactant and a buffer (Le, a crystallizing agent) and injecting the water solution into a vessel for crystallization equipped with a stirring system, wherein the surfactant in this step (2) is independently at least one ingredient selected from the group consisting of polysorbate 80, polysorbate 20, polyoxyethylene hydrogenated castor oil 50, polyoxyethylene hydrogenated castor oil 60, poloxamer 188, polyoxyethylene castor oil, benzalkonium chloride and sodium lauryl sulfate, step (3): adding the solution of the active ingredient to the crystallizing agent in the vessel for crystallization while circulating the solution (or the suspension solution) in the vessel for crystallization via a bypass pathway equipped with a pump which (i) is connected to the vessel for crystallization, (ii) can make the solution in the vessel for crystallization circulated, and (iii) can pressure the solution, step (4): collecting a crystal precipitated in the vessel for crystallization from the solution (or the suspension solution) in step (3) through a filter, and step (5): preparing a water solution comprising a surfactant, a buffer, an isotonic agent and water for injection (i.e. a vehicle solution), and then injecting the water solution into the crystal of the active ingredient prepared in step (4) and mixing them to prepare a suspension formulation.

44. The composition of claim 42 or 43 wherein the crystal is a cubic crystal.

* * * * *